US009421555B2

United States Patent
Lee et al.

(10) Patent No.: US 9,421,555 B2
(45) Date of Patent: Aug. 23, 2016

(54) NON-LINEAR MAGNETOPHORETIC SEPARATION DEVICE, SYSTEM AND METHOD

(75) Inventors: Gil Lee, Dublin (IE); Peng Li, Dublin (IE); Mark Platt, Loughborough (GB); Gemma Cannon, Dublin (IE)

(73) Assignee: University College Dublin, National University of Ireland, Dublin (IE)

( * ) Notice: Subject to any disclaimer, the term of this patent is extended or adjusted under 35 U.S.C. 154(b) by 0 days.

(21) Appl. No.: 13/809,091

(22) PCT Filed: Jul. 7, 2011

(86) PCT No.: PCT/EP2011/061550
§ 371 (c)(1),
(2), (4) Date: Sep. 24, 2013

(87) PCT Pub. No.: WO2012/004363
PCT Pub. Date: Jan. 12, 2012

(65) Prior Publication Data
US 2014/0021105 A1    Jan. 23, 2014

(30) Foreign Application Priority Data
Jul. 8, 2010    (GB) .................................. 1011518.6

(51) Int. Cl.
*B03C 1/02*    (2006.01)
*B03C 1/032*    (2006.01)
*B03C 1/24*    (2006.01)
(Continued)

(52) U.S. Cl.
CPC .................. *B03C 1/02* (2013.01); *B03C 1/032* (2013.01); *B03C 1/24* (2013.01); *B03C 1/288* (2013.01); *G01N 27/44756* (2013.01); *B03C 2201/18* (2013.01); *B03C 2201/24* (2013.01); *B03C 2201/26* (2013.01)

(58) Field of Classification Search
CPC .......... B03C 2201/24; B03C 2201/26; B03C 1/032; B03C 1/24; B03C 1/288; B03C 2201/18; B03C 1/02; G01N 27/44756
See application file for complete search history.

(56) References Cited

U.S. PATENT DOCUMENTS

2003/0044832 A1    3/2003    Blanenstein
2004/0018611 A1    1/2004    Ward et al.
(Continued)

FOREIGN PATENT DOCUMENTS

| EP | 2191895 A1 | 2/2012 |
|---|---|---|
| WO | 2008156688 A2 | 12/2008 |
| WO | 2008156688 A3 | 12/2008 |

OTHER PUBLICATIONS

Dynamic bioprocessing and microfluidic transport control with smart magnetic nanoparticles in laminar-flow devices Published online Mar. 16, 2009; Lai et al.*

(Continued)

*Primary Examiner* — Shogo Sasaki
(74) *Attorney, Agent, or Firm* — HolzerIPLaw, PC

(57) ABSTRACT

A flow enhanced method and system for flow non-linear magnetophoresis (F-NLM) is described. By tuning an external field frequency and the flow rate the migration velocities of different bead types may be caused to differ by several orders of magnitude over an extended range of frequencies to allow for separation of particles. Use of such efficiency in separation in bio-separation and similar assays is described.

44 Claims, 20 Drawing Sheets

(51) Int. Cl.
*B03C 1/28* (2006.01)
*G01N 27/447* (2006.01)

(56) References Cited

U.S. PATENT DOCUMENTS

2008/0124779 A1 5/2008 Oh et al.

2009/0220932 A1 9/2009 Ingber et al.

OTHER PUBLICATIONS

International Searching Authority Search Report and Written Opinion, PCT/EP2011/061550, May 6, 2012.

Yellen et al., "Traveling wave magnetophoresis for high resolution chip based separations", XP-002510110, Oct. 17, 2007, 8 pages.

* cited by examiner

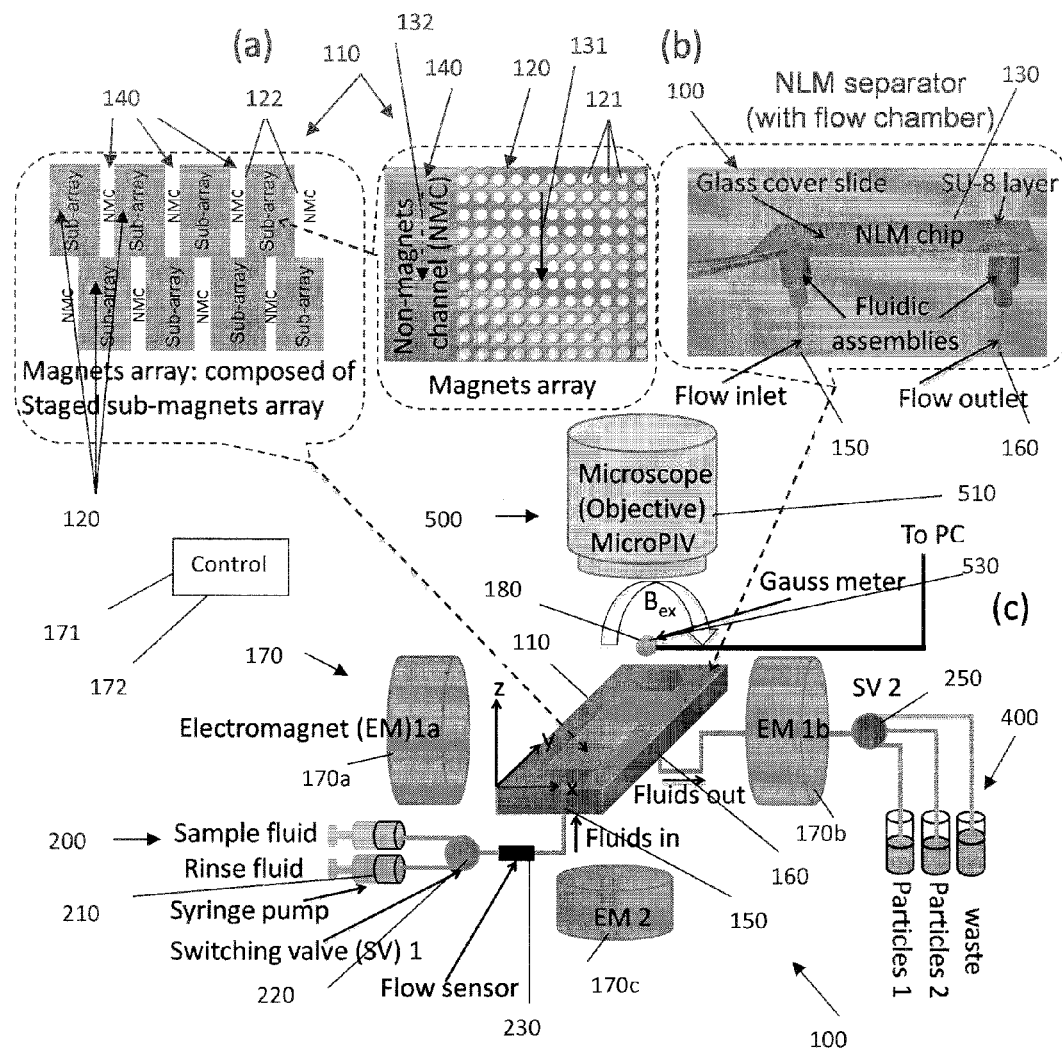
Figs. 1(a), (b) and (c)

Example 1: Separation of rare cell by using magnetic beads

Example 2: Separation of rare cell-virus-protein for diagnostics by using double magnetic beads Example 3: Separation of rare cell-virus-protein for diagnostics by using nonmagnetic-magnetic beads Example 4: Separation of rare cell-virus for diagnostics by using magnetic beads Example 5: Separation of rare cell-virus for diagnostics by using nonmagnetic-magnetic beads

NON-LINEAR MAGNETOPHORETIC SEPARATION DEVICE, SYSTEM AND METHOD

PRIORITY CLAIM

The present application is an U.S. 371 National Phase Patent Application and claims benefit of Patent Cooperation Treaty application No. PCT/EP2011/061550 entitled "Non-linear Magnetophoretic Separation Device, System and Method" and filed on 7 Jul. 2011 and having priority date of 8 Jul. 2010, which is incorporated herein by reference in its entirety.

FIELD

The present invention relates to non-linear magnetophoretic (NLM) separations and in particular a separation device and system for flow enhanced non-linear magnetophoretic (F-NLM) separations and a related method.

BACKGROUND

Bio-separation describes techniques used for determining the molecular state of a cell, or whole organism. Currently, bio-separation is often performed using liquid chromatography, electrophoresis or centrifugation, which achieves separation by transporting an analyte relative to a stationary phase based on a physical or chemical property, such as surface chemistry, size, charge, or mass density. Although these techniques are able to separate analytes with a high resolution they are slow and often difficult to implement.

Another bio-separation technique is linear magnetophoresis. In this technique a very strong magnetic field and field gradient are typically applied to effect separation. However, in known linear magnetophoresis, the magnetic particles often coagulate to form undetectable complexes such as chains, which can make it difficult to perform multiple separations on different particles.

There is therefore a need to address these and other problems and limitations of prior art separation devices and methods.

SUMMARY

These and other problems are addressed in accordance with the present teaching by a flow enhanced non-linear magnetophoretic separator. Such a separator is typically provided a chip based device comprising first and second fluid paths which differ from one another in the nature of the magnetic field that is experienced by particles travelling through those fluid paths. By specifically targeting the magnetic field to a specific type of particle it is possible to preferentially target particles within one of the two fluid paths. This can be used to separate particles of a first and second type. According to a first aspect the invention provides a magnetophoresis chip assembly device for use in separating first and second particle types provided within a sample, the device comprising an inlet for introduction of a flowing sample, the sample once introduced having a flow path in a first direction through the device, the flow path comprising first and second fluid paths in fluid communication with one another, the assembly comprising a magnetic array provided proximal to the first fluid path such that particles within the sample operably experience an induced magnetic field causing a retention of particles of the first type within the first fluid path, the particles of the second type being transported to the second fluid path thereby effecting a separation of the first and second particle types.

Preferably, the device is configured such that operably the particles of the second type are transported to the second fluid path in a direction substantially perpendicular to the flow path. In one embodiment the device is configured for use with an external rotating magnetic field, and wherein the induced magnetic field is a combination of a response of the particles to both the magnetic array and the external rotating magnetic field.

The second fluid path may define a non-magnetic flow channel through the device. Alternatively a second magnetic array provided proximal to the second fluid path. In one embodiment the magnetic field induced by the first magnetic array is different to that induced by the second magnetic array. The magnetic array may comprise a plurality of individual micro-magnet arrays. The device may comprise different individual magnetic arrays are configured to operably provide separation of particles of different type simultaneously at the same frequency of rotation of the external magnetic field. The magnetic arrays may comprise different periodic parameters and/or micro-magnets of different dimensions. The device may comprise non-magnetic separation channels provided adjacent or between multiple individual magnetic arrays.

The chip assembly may comprise an outlet provided downstream of the inlet. Each of the first and second fluid paths may comprise an individual inlet. The individual inlets are coupled to a common inlet of the device. The outlet may provide separate outlets to the first and second fluid paths. The device may be configured to receive a sample flow and a carrier flow, the sample flow operably being directed through the first fluid path and the carrier flow operably being directed through the second fluid path.

Preferably, the particles comprise super-paramagnetic particles. The super-paramagnetic particles may be formed from complex sample mixtures. The present teaching also provides specific types of particles that are configured to be advantageously useable within the context of a magnetic separator. For example, in a first arrangement a magnetic particle covalently attached to a nucleic acid probe forming complexes with a second fluorescent particle also covalently attached to a nucleic acid probe may be provided. A second example is a magnetic particle covalently attached to a nucleic acid probe forming complexes with a second magnetic particle also covalently attached to a nucleic acid probe. A third example is a streptavidin coated magnetic particle coupled to a biotinylated nucleic acid probe forming complexes with a second fluorescent or magnetic particle also covalently attached to a nucleic acid probe. It will be appreciated that in this context:

The magnetic and fluorescent particles can be of any size
The fluorescent particles can be of any fluorescence
The nucleic acid probes can be DNA or RNA
The nucleic acid probes can contain degenerate bases
The nucleic acid probes can be of varying length According to a further aspect, there is provided a system for flow enhanced non-linear magnetophoretic separation of first and second magnetic particles of a sample, comprising: a chip assembly device according to the present specification, and magnetic means operable on the chip assembly to apply an external rotating magnetic field.

In one embodiment, the magnetic means comprises a frequency control whereby the frequency of the applied external rotating field may be varied. Preferably, the frequency control is useable in separating the first and second particles. Preferably, the magnetic means is operable to generate a travelling magnetic field. The system may be configured to direct the travelling magnetic means in a direction substantially perpendicular to the flow.

Preferably the system comprises a flow control for controlling the rate of flow of a sample in the device.

In one embodiment, the particles of the first and second type are responsive to a predefined frequency of operation of the rotating magnetic field, the particles of the first type having a critical frequency, $\omega_c$ at which particles of the first type begin to be trapped in the magnetic array, the particles of the first type having a threshold frequency $\Omega_t$ at which a majority of particles of the first type are trapped in the magnetic array, the magnetic means being tuneable to vary to allow selection of at least one of the critical and threshold frequency. Preferably, the particles of the second type have a different critical and threshold frequency to the particles of the first type. Preferably, the threshold frequency is greater than the critical frequency for each of the particles of the first and second types. Preferably the frequency of operation of the rotating magnetic field of the magnetic means effects transport of the particles from the first fluid path to the second fluid path. In one embodiment the frequency $\omega$ of rotation of the external magnetic field is greater that the critical frequency $\omega_c$ of the particles of the first type and less than the critical frequency $\omega_c$ of the particles of the second type.

In one embodiment the system comprises means for applying a non-magnetic force to particles of the second type in the second fluid path to effect their transport and separation. In one embodiment the system comprises flow control operable to vary the rate of flow of a sample through the device. The flow control means is operable to control the rate of flow applied to the first fluid path and/or in the second fluid path. In one embodiment each of the flow control and the magnetic control effects a variance in an induced force on the particles within the device. Preferably, each of the flow control and magnetic control are tuned to effect separation of the particles of the first and second types.

In one embodiment the frequency of rotation of the external magnetic field is controllable to effect transport of the particles of the second type to an intermediary region adjacent to each of the first and second fluid paths in the direction of the rotating magnetic field. In another embodiment the rate of flow in the second fluid path is operably controllable to provide a hydrodynamic force to effect movement of the particles of the second type which have been transported to an intermediary region adjacent to each of the first and second fluid paths. In a further embodiment the frequency of rotation of the external magnetic field is controllable to operably provide that particles of the second type oscillate in phase with the external magnetic field at the intermediary region.

Alternatively, the system may comprise means for providing a hydrodynamic, electro-kinetic, gravitational, or centrifugal force to the second fluid path to effect transport and separation of particles of the second type.

In one embodiment, the flow control effects a variance on the flow based on properties of the particles of the first and/or second type.

The system may further comprise a sensor or detector means configured to sense or detect particles. The sensor or detector means may comprise an impedance sensor or micro-coulter detector or optical microscope. The sensor or detector means may be configured to induce a minimal local magnetic field. The system may further comprise monitoring means for monitoring operation of the system. The monitoring means may comprise a microscope or Gauss-meter or pressure meter.

In one embodiment, the system may be configured for use in-line with for example a linear magnetophoresis separator, the linear magnetophoresis separator effecting a first separation of particles. The system may also be used with one or more detectors for use in providing analysis of the separated particles. One example of such a detector is a fluorescent detector which may be usefully employed where the particles being detected are fluorescently tagged or otherwise luminesce on excitation. In such an arrangement the flow enhanced non-linear magnetophoretic separator is typically provided between each of the linear magnetophoretic separator and the detector.

The particles may be provided in the form of micro-beads. The particles may be functionalised prior to introduction into the device that forms the flow enhanced non-linear magnetophoretic separator.

According to a further aspect there is provided a method of non-linear magnetophoretic separation comprising Providing a separation system comprising a magnet array and a non-magnetic separation channel in first and second fluid paths, Introducing a sample comprising micro-beads of a first and second type into the system, Applying a rotating magnetic field proximate to the magnet array, Controlling the frequency of the rotating magnetic field, and wherein the frequency of rotation of the external magnetic field and the flow rate are tuned to provide separation of said micro-beads of said second type from said micro-beads of the first type.

In one embodiment the method comprises controlling flow in first and second fluid paths. Preferably, magnetic field is operable at a frequency of rotation above the critical frequency of the micro-beads of a first type and below a threshold frequency of micro-beads of a second type to effect a separation thereof. Preferably, the method comprises the step of trapping the micro-beads of the first type on the magnet array. Preferably the method comprises transporting micro beads of the second type across the magnet array to the non-magnetic separation channel adjacent an edge of the magnet array.

In one embodiment the method comprises applying a non-magnetic force to transport micro-beads of the second type downstream from said edge of the magnet array to effect separation of said micro-beads of the second type. In another embodiment the method comprises applying flow and controlling the rate of flow such that the resultant hydrodynamic forces effect a transportation and separation of said micro-beads of the second type. Preferably the rate of flow is controlled such that the induced hydrodynamic force is in a range less than the force needed to displace the micro-beads of the first type trapped on the magnet array and greater than that need to displace said micro-beads of the second type which have been transported to the edge of the magnet array. In another embodiment the method comprises, after the micro-beads of the second type have been separated from the micro-beads of the first type and transported downstream by flow, the reduction of the frequency of rotation to a frequency below the critical frequency of the micro-beads of the first type to effect transport by non-linear magnetophoresis of the micro-beads of the first type to the edge of the micro-magnet array and transport of the micro-beads of the first type from said edge of the micro-magnet array downstream. In a further embodiment after micro-beads of the second type have been separated, the rate of flow is controlled such that the induced hydrodynamic force in the magnet array is sufficient to displace and transport said micro-beads of the first type downstream. In one embodiment the method further comprises collecting or counting or analysing said micro-beads of the first and second type that have been separated. Preferably the frequency of rotation and flow rate are controlled to provide a continuous separation.

According to a fourth aspect, there is provided a system and method of flow enhanced non-linear magnetophoretic separation for rare cell separation for translation medicine applications, for example stem cell separation from a complex fluid sample. The sample preferably comprises cell-magnetic particles complexes to be separated. The method further comprises the step of attaching one or more antibodies or receptors of choice to super-paramagnetic particles prior to introducing the sample to a flow enhanced non-linear magnetophoretic separator.

According to a fifth aspect there is provided a system and method of rare cell-virus-protein separation for diagnostics, for example to separate neonatal white blood cells from a maternal blood sample, employing a flow enhanced non-linear magnetophoretic separation step. Such a method may include multiple steps either up and/or downstream of the flow enhanced non-linear magnetophoretic separation step. For example the methodology may comprise a step of attaching analytes of interest to be separated to selected magnetic particles of defined size. These attached analyte/magnetic particles may then be aggregated through use of an aggregation technique to drive the clustering of magnetic particle around analytes. Such aggregation may be effected using linear magnetophoresis techniques. The provision of an aggregate of multiple analyte/magnetic particle to a non-linear magnetophoretic separator provided downstream of the aggregator may be usefully employed to increase the ease of identification of complexes.

According to a sixth aspect there is provided a system and method employing flow enhanced non-linear magnetophoretic separation for rare cell-virus separation for diagnostic purposes. Such a system and methodology may use non-magnetic-magnetic particles, in a direct protein configuration for example, to separate neonatal white blood cells from a sample of maternal blood. The method may comprise the step of preparing the sample for separation by attaching one or more antibodies or receptors of choice to magnetic or non-magnetic particles of defined size. Preferably the magnetic particles and non-magnetic particles are of substantially uniform size and magnetization. In a preferred arrangement the non-magnetic particles comprise fluorescent particles configured to allow an analyte to be tagged for a second degree of sensitivity in multiplexed sensing. The sample may be identified through the formation of magnetic-nonmagnetic complexes.

According to a seventh aspect there is provided a system and method using flow enhanced non-linear magnetophoretic separation for rare cell-virus separation for diagnostic purposes. Such a system and methodology may use small magnetic particles and a direct protein configuration. Preferably the method comprises the step of attaching one or more antibodies or receptors of choice to magnetic or nonmagnetic particles. The method may further comprise the step of mixing the antibodies with the cells prior to attaching the magnetic particles to the cells using a protein or similar receptor. In a preferred embodiment the method further comprises the step of aggregating particles prior to the step of flow enhanced non-linear magnetophoretic separation to drive the clustering of magnetic particles around the cells.

According to an eighth aspect, there is provided a system and method of flow enhanced non-linear magnetophoretic separation for rare cell-virus separation for diagnostics using magnetic-nonmagnetic particles in a molecular configuration. Preferably the method comprises the step of attaching one or more antibodies, receptors, or DNA oligonucleotides to magnetic or nonmagnetic particles. Preferably the particles are uniform in physical properties, i.e., magnetization, color and size. Preferably the method comprises an initial separation step whereby techniques such as linear magnetophoresis are used to clean-up the sample for DNA extraction. After this initial clean-up step the DNA may be extracted, hybridized with specific oligonucleotides and then reacted with a second set of particles prior to being introduced into a flow enhanced non-linear magnetophoretic separator. Preferably the sample may be identified through the formation of magnetic-magnetic or magnetic-optical complexes.

According to a ninth aspect, there is provided a chip assembly device comprising first and second fluid paths in fluid communication, the first fluid path comprising a first magnetic field and the second fluid path comprising a second different magnetic field. The second different magnetic field may be a zero magnetic field.

Preferably, the first fluid path comprises a first magnet array. In one embodiment, the device is configured for use with an external rotating magnetic field and the first magnetic field is defined by the interaction of an external rotating magnetic field and the first magnet array. Preferably the first magnetic field is different from the second magnetic field. Preferably, the second fluid path may comprise a non-magnetic separation channel and the second magnetic field is defined by the interaction of an external rotating magnetic field on the non-magnetic separation channel. Alternatively, the second fluid path may comprise a second magnet array. Preferably, the magnet array may comprise a micro-magnet array or multiple discrete micro-magnet arrays. The first and second fluid paths are preferably provided in a flow chamber. The chip assembly may further comprise a flow control means for controlling the rate and direction of flow in the first and second fluid paths. The chip assembly may comprise an inlet means. The chip assembly may comprise an outlet means. Preferably the flow control means operable to provide flow in the first and second fluid paths in a direction transverse to the direction of the first and/or second magnetic fields. Preferably the chip assembly is configured to provide separation of micro-beads of a first and second type of a sample. Preferably, the frequency of rotation of the external magnetic field is controllable to effect a transport of the micro-beads of the second type to an edge of the first magnet array in the direction of the rotating magnetic field. Most preferably micro-beads of the second type are transported across the first magnet array of the first fluid path to the second fluid path. In one embodiment, the frequency of rotation $\omega$ of the external magnetic field is less than the critical frequency $\omega_c$ for the micro-beads of the second type on the first magnet array. In one embodiment, the frequency of rotation of the external magnetic field is controllable to operably provide that micro-beads of the second type oscillate in phase with the external magnetic field at the edge of the first magnet array. In a further embodiment a non-magnetic force is applied to micro-beads of the second type in the second fluid path to effect transport and separation of said micro-beads of the second type.

BRIEF DESCRIPTION OF THE DRAWINGS

The present invention will now be described with reference to the accompanying drawings in which:

FIG. 1(a) is an illustration of fabricated non-linear magnetophoretic (NLM) magnet array and configuration of an F-NLM chip; FIG. 1(b) is an illustration of a fabricated F-NLM separator with flow chamber, in which a F-NLM chip is encapsulated and FIG. 1(c) is a schematic system set-up for F-NLM separation;

FIG. 2(b)-A to H illustrate a finite element calculation of the magnetic field (normalized B=√B.B) on the edge of a magnet array in a y-plane through the center of the micromagnets as a function of external magnetic field angle. The magnetic particles tend move towards region of maximum magnetic field. In the images, the dark colour is the low field region and the light colour is the high field region.

FIG. 5(a) shows a system having a flow chamber with two inlets and outlets and one form of micro-magnet array; FIG. 5(b) shows a system having a flow chamber with four inlets and outlets respectively and four different forms of magnet arrays;

FIGS. 6(a) and 6(b) relate to FIG. 1, FIG. 6(c) relates to FIG. 5(a) and FIG. 6(d) relates to FIG. 5(d);

FIG. 9A shows the External magnetic field rotation from 0-135°. FIG. 9B shows External magnetic field rotation from 180-315°. Bottom: Position of micro-magnets. FIG. 10A is an illustration of separation of rare cells using magnetic beads; FIG. 10B is an illustration of separation rare cell virus proteins using double magnetic beads; FIG. 10C is an illustration of separation of rare cell virus proteins using non-magnetic-magnetic beads; FIG. 10D is an illustration of separation of rate cell virus for diagnostics using magnetic beads and FIG. 10E is an illustration of separation of rare cell virus using non-magnetic-magnetic beads.

DETAILED DESCRIPTION OF THE DRAWINGS

Figure 2A:
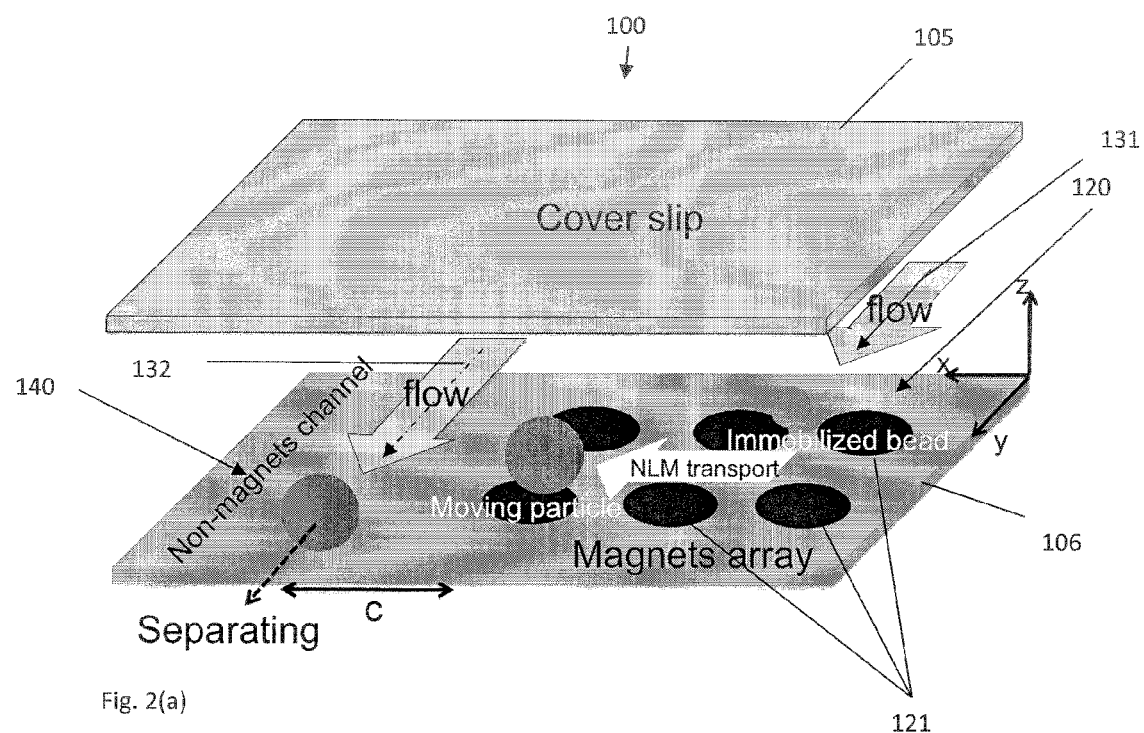
FIG. 2(a) is a schematic of an applied laminar flow at the edge of the magnet array to separate the magnetic particles whereby particles which have low NLM critical frequency are immobilized and stay on the magnet array.

Referring to the attached drawings and initially in particular FIGS. 1(a) to (c), and FIGS. 2 and 3 there is provided a separation system 100 comprising a chip assembly device 110 for performing flow enhanced non-linear magnetophoretic (F-NLM) separations of analyte particles in a sample. It will be appreciated that the specifics of this separation system are provided to assist in an understanding of the present teaching and in no way should be construed as limiting the teaching to this example.

The separation system 100 comprises a magnetophoresis chip assembly device 110 for use in separating first and second particle types provided within a sample. The chip assembly device 110 comprising an inlet means 150 for introduction of a sample. The components of the chip assembly device are provided embedded in a flow chamber 130. The sample is introduced as a flowing sample, and once introduced has a flow path in a first direction through the device. The flow path preferably comprises a first fluid path 131 and a second fluid path 132 in fluid communication with one another. In the example shown, each of the first and second fluid paths are located side by side with one another. They are, in this exemplary configuration co-extending within the device. In this example it will be appreciated that the flow path is bifurcated into first and second fluid paths.

The device 110 comprises a magnetic array 120 provided proximal to a fluid path. In the exemplary arrangement shown, the first fluid path is provided proximal to and is overlain on an array comprising a plurality of individual or discrete micro-magnet arrays 120. By providing the first fluid path proximal to the magnetic array 120, particles travelling within the first fluid path may experience an induced magnetic field. By suitably configuring the nature of the field to the specifics of the particles, it is possible to target specific particles travelling within a fluid flowing through the first fluid path.

The second fluid path differs from the first in the nature of the magnetic field that may be experienced by particles travelling within this fluid path. In an exemplary arrangement no magnetic array is provided proximal to the second fluid path such that it defines a non-magnetic flow channel 140. The second fluid path/non-magnetic flow channel may be provided as a single or plurality of individual channels 140.

The chip is configured to cooperate with a magnetic module 170 which is provided as part of the overall separation system. The magnetic module 170 preferably comprises electromagnets, and is configured to operably generate an external magnetic field. The magnetic field may be considered an external magnetic field and applied proximate to or around the magnetic arrays 120. The external magnetic field ($B_{ext}$) is operably provided as a rotating or travelling magnetic field. The system includes a magnetic field controller 171 including a frequency controller 172 for controlling the frequency of rotation of the magnetic field, as required. In the exemplary arrangement of FIG. 1, the rotating magnetic field $B_{ext}$ is provided by a magnetic module 170 comprising three electromagnets 170a, 170b and 170c. The frequency control is useable in separating the particles travelling within a fluid flow through the device.

The system comprises an inlet means 150 and flow controller 200. In the exemplary arrangement of FIG. 1, the inlet means comprises a single inlet for a sample fluid and a rinse fluid. The flow controller 200 may include a syringe pump 210, a switching valve 220, and a flow sensor 230. The flow controller is operable to control the rate of flow of a sample through the device. The flow controller may be operable to control the rate of flow applied to the first and/or second fluid path.

The flow sensor 230 may be provided being configured to monitor the flow rate in the flow chamber 130 in real time. Preferably the flow sensor 230 is integrated into the chip assembly or system. Flow, transport, and the behaviour of particles within the separation system and the separation process may be observed and recorded using suitable sensor or monitoring means 500. For example a microscope or fluorescent microscope 510 may be provided. The profile of flow may be monitored by using for example a micro particles image velocimetry system. The magnetic field around the chip 110 may be monitored and/or recorded by suitable monitoring means such as a Gaussmeter 530. The system 100 or device 110 may further include one or more pressure meters to monitor flow rates; i.e., pressure drop across channels provided. It is further noted that the sensor or detector means could be configured to sense or detect change in the electrical, magnetic, or optical properties of the channel. It will be appreciated that this could be done in different ways. Requirements for the sensor or detector include that it should be fast and able to count many particles. The sensor or detector is preferably configured to induce a minimal local magnetic field.

The arrangement and configuration of the system and chip assembly device 110 and the magnetic array 120 in the first fluid path is such that particles within an introduced sample operably experience an induced magnetic field configured to cause a retention of particles of a first type within the first fluid path 131 or on the magnetic array 120. The particles of a second type are transported to the second fluid path 132 or non-magnetic separation channel 140 thereby effecting a separation of the first and second particle types of the sample. Operably, the particles of the second type are preferably transported to the second fluid path in a direction substantially perpendicular to the flow path through the device. The chip assembly device 110 is configured for use in a system with an external rotating magnetic field $B_{ext}$ as described above and the induced magnetic field in the chip assembly device is a combination of the response of the particles to both the magnetic array and the external rotating magnetic field. In order to provide a separation of the particles of the first and second types it will be appreciated that these particles desirably differ in their response characteristics to the induced magnetic field; the particles of the first type being more attracted than those of the second type. In this way the particles of the first type are more likely to be retained within an area defined by the first fluid path, and those of the second type will migrate away from the first fluid path into the second fluid path.

The flow of particles of a sample to the separation system 100, chip assembly 110 and the flow chamber 130 is provided via an inlet means 150. The chip assembly 110 and flow chamber 130 further comprise an outlet 160. The separation system 100 may include flow control means 200 for controlling the flow rate of a sample there through, as required. The direction of flow or flow path in the flow chamber 130 of the exemplary arrangement of FIG. 1 is downstream between the inlet 150 and outlet 160. The axis of flow is, in this example, provided normal to the orientation of the external magnetic field $B_{ext}$. An outlet separator or analysis means 400 may be included to provide for final separation and/or countering of beads and/or analytes of a sample. It will be appreciated that flow may be applied continuously or discontinuously as required or as appropriate for a particular separation. Each of the first and second fluid paths of the device may comprise an individual inlet. It will be appreciated that the outlet may provide separate outlets to the first and second fluid paths. The device 110 may be configured to receive a sample flow and a carrier flow, (for example as shown and later described with reference to FIG. 5A), the sample flow operably being directed through the first fluid path and the carrier flow being directed through the second fluid path.

The magnetic arrays 120 are provided preferably as multiple discrete or individual micro-magnet arrays on the flow chip assembly 110. Micro-magnet arrays 120 of different form or having different properties may be provided or may be configured for the capture of different analytes. For example, the dimensions of the micro-magnets of the arrays or sub-arrays may be different or the separation of the micro-magnet of the arrays or sub-arrays may be different. As shown in FIG. 1, the micro-magnet arrays may comprise multiple sub-magnet arrays. The magnet arrays or sub-magnet arrays may have different periodic characteristics, and may be provided or arranged on the same chip to support and implement multiple separations simultaneously. Preferably, the different individual magnetic arrays are configured to operably provide separation of particles of different types. This separation is desirably achieved simultaneously under the same frequency of rotation of the external magnetic field. The magnets are useable in creation of an effective travelling magnetic field wave which combines with the external rotating field. In the description, the terms magnet array, magnetic array, micro-magnet array and sub-array have been used interchangeably.

In the exemplary chip assembly 110, ten micro-magnet arrays/subarrays 120 are arranged in two offset or staggered rows of five micro-magnet arrays 120. Non-magnetic flow channels 140 are arranged between the longitudinal edges 122 of the micro-magnet arrays 120. The non-magnetic separation channels 140 in the first row of micro-magnet arrays 120 are in-line with the lateral ends of the micro-magnet arrays 120 in the second row. The second row of micro-magnet arrays is arranged downstream in the flow chamber from the first row. The micro-magnet arrays may comprise periodic arrays. The configuration of the exemplary FIG. 1 provides a highly efficient separation based on the staged two columns of sub-magnetic arrays. Similarly, multiple staged sub-magnet columns may be used for multiple separations with high efficiency.

Figure 3A:
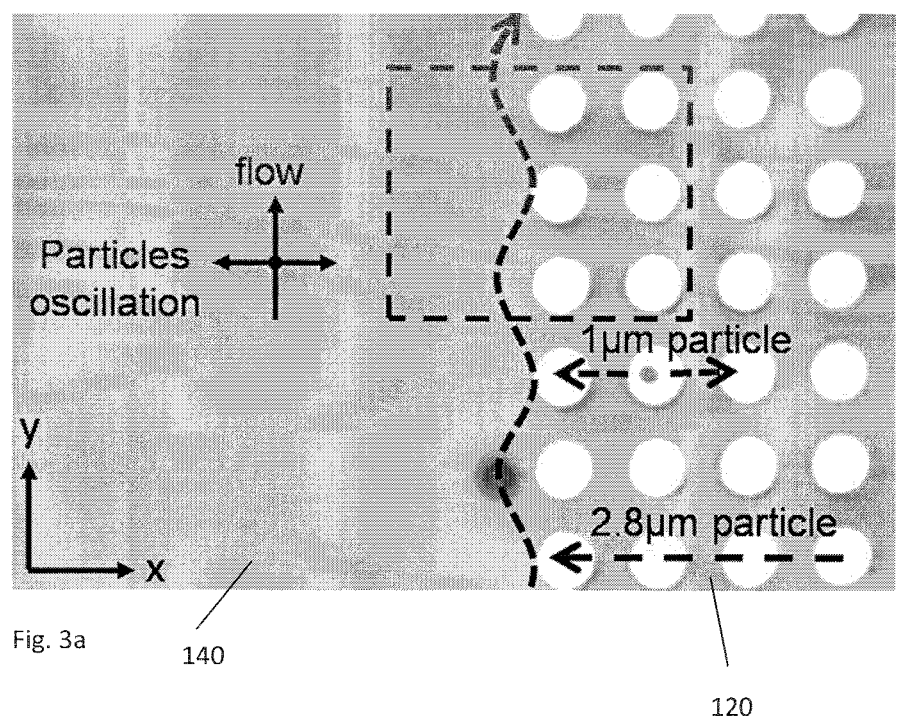
FIG. 3a is a top-view of the micro-magnet array (white circles) with 1 and 2.8 μm diameter super-paramagnetic particles (black circles). The micro-magnetic arrays have been magnetized in the x-direction. The external magnetic field is rotated about the y-axis and a hydrodynamic flow is produced in the y-direction. The motion of the particles under a 9 Hz rate of frequency of rotation of the external field has been shown on the figure with dashed lines. The 2.8 μm particles move to the edge of the array and then along its edge. The 1 μm particles are locked on the array.

Referring to the exemplary magnetic array of FIG. 3a, a micro-magnet array 120 may be comprised of circular magnets 121 arranged in a square lattice. Such magnets may be of dimensions of the order of 5.0±0.1 μm diameter arranged in a square lattice with 8.0±0.1 μm center-to-center distance. The form or layout of the micro-magnet arrays 120 may be varied, as required, depending for example, on the types of separations to be provided or on the analytes of interest in a particular separation. In the exemplary arrangements, the micro-magnets are of substantially circular form, however, micro-magnets of suitable different form or geometric shape, may also be used. Examples of such alternatives include rectangular, bar, and triangle magnets. Each configuration may be arranged to provide different resolution and efficiency of separation, as required.

Figure 3B:
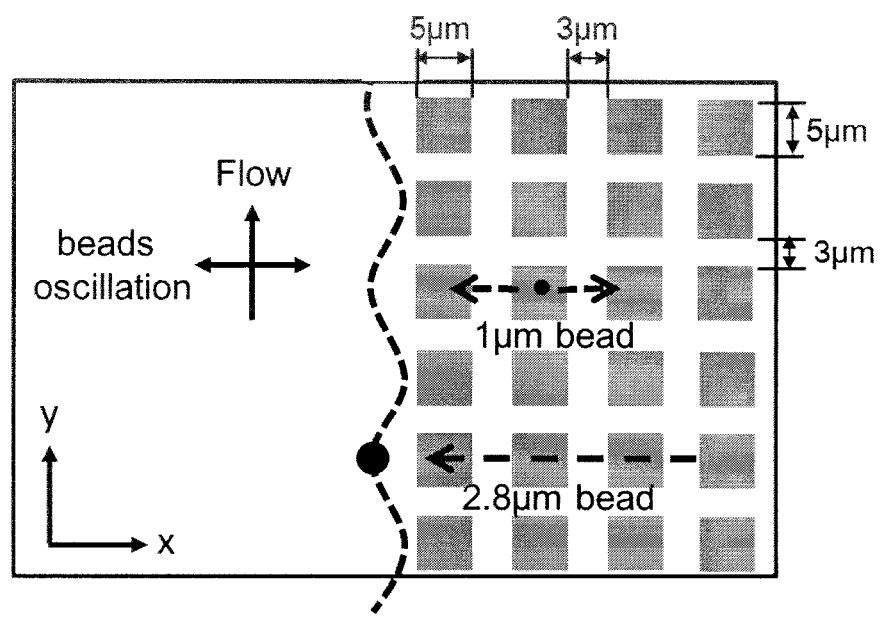
FIG. 3b is a similar view for a square based magnet array.

It was found during separation in F-NLM, that the immobilized particles on a micro-magnet array have to be held on the micro-magnet array in flow direction at the same time as the separated particles travel transversally to the edge of micro-magnet array and are then being swept downstream by flow. A large holding force is required for quick separation in high flow rate flow. The rectangular or square shapes of micro-magnets shown in FIG. 3b are usefully employed to increase the holding force and stabilize the particles movement in the flow direction during the separation. It has been found that potential wells for square micro-magnets are deeper than that for circular micro-magnets in the y-direction, the flow direction. When the phase of external magnetic field is 90° and 270°, the sizes of potential wells for circular micro-magnets are larger than that for square micro-magnets. In this case, the magnetic particles could be tightly detained into potential well and cannot be moved in y direction for square micro-magnets as compared with circular micro-magnets.

As shown in the exemplary FIG. 1, the non-magnetic flow/separation channels 140 may be provided between or adjacent to the multiple individual micro-magnet arrays. In this way multiple fluid paths of a first and second type may be provided. The non-magnetic flow/separation channels 140 are configured to allow specific proportions of separated particles pass subsequent to their separation from an adjacent magnetic array. Within the context of the present teaching many techniques may be employed to provide for this separation. For example the remaining particles could be separated from the magnets array by applying high flow rate flow or by varying the frequency of the applied magnetic field.

The surface properties of non-magnetic channels may be modified by using surface chemicals to reduce adhesion forces. It will be appreciated that such modification may increase the flow rate of particles through this second fluid path. In a similar fashion a thin layer of Polyethylene glycol (PEG) or other suitable material may be coated on the surface of the micro-magnet array to reduce the adhesion between magnetic particles and the surface.

It will be understood that the device and system describe heretofore is particularly advantageously employed as a separation system or device for non-linear magnetophoretic (NLM) separation. In this context the particles that are introduced into the device include super-paramagnetic micro particles or micro-beads. Within the present specification the term beads is intended to define particles having dimensions on a nano or micro scale. It has been ascertained by the present inventors that super-paramagnetic particles with thick diamagnetic shells, such as silica, can be particularly usefully employed. An example of such a silica coated paramagnetic particle comprises a 200 nm thick silica shell provided about a super-paramagnetic core of 600 nm diameter. Typically, in external magnetic fields, super-paramagnetic particles form chains, which align with the direction of the external magnetic field, due to dipole-dipole interactions. In magnetophoresis, the configuration of chains can decrease the separation efficiency. Compared with Dynabeads Myone, silica shell particles have weaker particle-particle magnetic interaction in external magnetic fields. The silica shell magnetic particles could increase the separation efficiency for F-NLM due to fewer chains formed and the longer time to form chains in magnetic field.

However, irrespective of the specifics of the formation of the particles such particles may be functionalized with antibodies or DNA oligonucleotides to form magnetic complexes specific for a given pathogen. The super-paramagnetic particles or micro-particles of for example, a first and second type are responsive to and therefore may be separated by the application of different critical frequencies of the external rotating magnetic field. The critical frequencies and threshold frequencies for different particles vary depending on the properties of the particles. These properties include, for example, size or magnetic moment. In the present specification super-paramagnetic micro-beads of a sample are alternatively referred to as micro particles, particles, micro-beads, beads and analytes. Example analytes include a dimer or sandwich assay in which, the analyte is bound between two magnetic particles. Another example comprises a magnetic particle bound to a non-magnetic particle, analyte. Such an example could be a bacteria or cell (e.g. a stem cell), bound to a magnetic particles or beads and a fluorescent particle. It is also possible to use magnetic particles of different colours to allow identification and resolution of analytes on the basis of colour. A system provided in accordance with the present teaching may also provide for the identification of particles of different colour or size for example by use of the heretofore described monitoring or sensor means.

The particles are typically provided in a solution and such solutions are normally buffered or constant pH or aqueous solutions. The solutions may be selected to avoid stickiness of particles. An exemplary sample having first and second different micro-beads is described in detail below.

Referring to the drawings and initially FIGS. 1, 2 and 3, in operation, the micro-magnets 121 of the arrays 120 are magnetized in the X direction. The external rotating or travelling magnetic field is rotated about Y axis and the flow is provided in the Y direction. The flow fields are provided normal to the orientation of the external magnetic field. The rotating magnetic field $B_{ext}$ is provided orthogonal to the axis of flow on the chip. While exemplary directions and relative directions of fields and flow are illustrated, it will be appreciated that suitable alternative arrangements may also be used.

In accordance with the present teaching a continuous flow across the micro-magnet arrays may be applied. By tuning the frequency of rotation of the external rotating fields and flow rate, specific particles of the sample can be continuously separated and collected. The flow is typically a laminar flow whose induced hydrodynamic forces are useable to control the behaviour of the particles in the flow direction. Transport of particles/beads on the micro-magnet arrays is controlled by controlling the frequency of the applied external magnetic field on the basis that different particles have different critical frequencies, as discussed in detail below.

It is possible within the context of the present teaching to manipulate the behaviour of the particles as they move within and are transported on the chip assembly. It is also possible to manipulate their behavior in specific predefined areas of the chip assembly. Examples of such areas include those defined by the magnet arrays and the non-magnetic channels. The system 100 provides control means 171 for controlling external magnetic field including control means 172 for controlling the frequency of rotation of the external magnetic field, and flow control means 200 for controlling the rate of flow in the flow chamber 130 and non-magnetic separation channels 140. In the system 100 there are further differences produced in the interaction of the external magnetic field on the micro-magnet arrays 120 and on the non-magnetic separation channels 140. The arrangement of the system 100 and chip assembly 110 is such that, control of frequency of the external magnetic field provides transport of the beads or particles on the micro-magnet arrays 120. Using the magnetic interaction selected particles may be trapped or immobilized on a micro-magnet array and selected other particles may be transported to the edge of the array. Using the influence of hydrodynamic flow on non-linear magnetophoresis in regions such as on a micro-magnet array, at the edge of a micro-magnet array, and in a non-magnetic separation channel is also of interest.

The separation system 100 and method may also be configured to take account of how relative forces namely, hydrodynamic flow and magnetophoretic transport, affect the movement of the particles within the device. It will be appreciated that these relative forces exert or induce a force on the particles and by controlling and varying these forces it is possible to manipulate the transportation of the particles within the device to provide effective separation. Separation using the exemplary separation system 100 and device 110 is based on non-linear magnetophoresis using continuous and/or discontinuous microarrays 120 in conjunction with a hydrodynamic flow. Transport of particles may be maintained at low fluid velocities. The flow enhanced non-linear magnetophoresis (F-NLM) provided in accordance with the present teaching allows for a continuous extraction of different types of particles based on, for example, variation in the size of and/or magnetic moments and/or magnetization of typical super-paramagnetic particles/beads.

In an exemplary method of use, particles of a first and second type are responsive to a predefined frequency of operation of the rotating magnetic field. The particles of the first type have a critical frequency $\omega_c$ at which particles of the first type are trapped in the magnetic array, and a threshold frequency $\Omega_t$ at which a majority of the particles of the first type are trapped in the magnetic array. The magnetic means 170 is tuneable to allow selection of frequency of rotation, and in particular of at least one of the critical and threshold frequency. The particles of the second type are desirably such as to have a different critical and threshold frequency to the particles of the first type. The threshold frequency of a particle of a particular type is greater than the critical frequency for the particles of that type. By using these differences in the response characteristics of the particles of the first and second type to an experienced magnetic field it is possible to use the frequency of operation of the rotating magnetic field to effect transport of the particles from the first fluid path to the second fluid path.

When the system is operated at a frequency of rotation above the critical frequency or threshold frequency of particles of the first type and below the critical frequency of particles of the second types, the particles of the second type are transported to an intermediary region adjacent to the first and second fluid paths in the direction of the rotating magnetic field while the particles of the first type are trapped in the magnetic array. In accordance with the configuration of the exemplary system 100, a force, here a hydrodynamic force is applied to effect movement and separation of the particles of the second type which have been transported to the intermediary region. The rate of flow in the second fluid path is operably controlled to provide a hydrodynamic force to effect the separation of particles of the second type as required. The rate of flow and the frequency of rotation of the external magnetic field are accordingly tuned to effect a separation of the particles of the first and second type.

The effects of the frequency of rotation of the external magnetic field and the rate of flow applied are described in greater detail as follows:

1. A translating periodic potential energy landscape is created by applying the external rotating magnetic field to the arrays 120 of micro-magnets. Super-paramagnetic particles exposed to the translating potential energy landscape provided move horizontally across the chip assembly or substrate at a rate that depends on the frequency of the external magnetic field w, as well as the characteristic properties of the bead or particle and the array. At low frequencies, the magnetic particles of the sample become locked into the potential energy landscape and are shuttled and move between adjacent magnets 121 of the magnetic array 120 with a speed proportional to the translation velocity of the landscape. As this frequency is increased, there is a point at which the particles can no longer remain in the local potential energy minima due to the hydrodynamic forces and they become immobilized on a micro-magnet. The frequency at which the particles begin to become immobilized, the critical frequency ($\omega_c$), is dependent on the size and magnetic moment of the super-paramagnetic particles. Thus as the frequency of rotation of the external magnetic field is varied, the behavior of magnetic particles on and near the micro-magnet arrays 120 in the travelling magnetic field varies. By tuning the rotating frequency of the external magnetic field specific magnetic particles/beads can be recognised on a micro-magnet array. The transport of the particles/beads on the micro-magnet arrays 120 is controlled by the control of the frequency of the external magnetic field.

Referring to the drawings and in particular FIGS. 3 and 4, an exemplary transport of magnetic particles or beads, is described in more detail. In the system 100 flow fields are normal to the orientation of the external magnetic field, as indicated in the drawings.

2. In the present system 100, the influence of hydrodynamic flow on non-linear magnetophoresis is important. While non-linear magnetophoretic transport remained unchanged at low fluid velocities on continuous micromagnet arrays, it was found that the magnetic beads could be displaced as the flow rate was increased. Surprisingly, the flow rate at which a bead was displaced from the micro-magnet array was not found to be strongly correlated with the size of the bead. The bead transport behaviour was also studied on or at the edge of continuous micro-magnet arrays. In the absence of flow, beads, for which $\omega<\omega_c$, oscillated between a point on the edge of the micro-magnets and a point in the area adjacent to the array. The oscillation was at an amplitude that decreased with increasing frequency. When flow was applied to the array, the beads moved in the direction of flow at a velocity that was determined by inter alia the bead properties, flow rate, and external magnetic field frequency. As illustrated in FIG. 3, beads translate along the edge of the micro-magnet array if $\omega$ is less than a threshold frequency, $\Omega_t$.

Surprisingly, the translation of the beads down the edge of the array was nonlinear in that the bead were observed to be trapped on the outer edge of the micro-magnet array at external field frequencies greater than this threshold frequency. The F-NLM (flow enhanced non-linear magnetophoresis) $\Omega_t$, frequency was found to be significantly larger than the NLM $\omega_c$ frequency for large beads, which results in a higher efficiency of separation. Further, F-NLM separates the beads based on their hydrodynamic size as they move along the edge of the array. Thus, F-NLM (flow enhanced non-linear magnetophoresis) enables efficient continuous separation of multiple analytes bound to super-paramagnetic beads from milliliter volume samples.

Accordingly the present teaching provides a system, a chip assembly and method providing a new mode of non-linear magnetophoresis (flow enhanced non-linear magnetophoresis F-NLM) that is capable of separating super-paramagnetic micro-beads from complex mixtures with high sensitivity to their size and magnetic moment. This separation method applies a rotating external magnetic field to an array of micro-magnets in a flow cell to produce a periodic magnetic field that translates across the surface perpendicular to a laminar flow field. In the absence of flow, beads whose critical frequency $\omega_c$, is less than the external magnetic field rotation frequency, $\omega$, move across the continuous micro-magnet array until they reached a region in which there are no micro-magnets. Beads at the edge of the micro-magnet array oscillate in-phase with the external magnetic field with an amplitude that decreases with increasing frequency until they reach a threshold frequency, $\Omega_t$, where a majority of them stop moving. Flow may be used to sweep beads for which the frequency experience<$\Omega_t$ downstream while leaving all the beads on the continuous array undisturbed. Surprisingly, magnetic beads for which $\omega_c>\Omega_t$ were trapped on all regions of the micro-magnetic array. Flow enhanced non-linear magnetophoresis (F-NLM) exhibits an improved range of separation frequencies as a result of the hydrodynamic separation of the beads at the edge of the array. This method enables efficient, multiplex, and continuous separation of super-paramagnetic beads based on size and magnetization, which clearly is useful in providing and developing chip based diagnostic assays and bio-separation technologies.

Referring to the drawings and in particular FIGS. 1, 4(a) and 4(b) and 5(a) and 5(b), it is noted that sample particles separated at specific frequencies may then be collected. This collection may be facilitated using, for example, a valve manifold or switching valve 250 on the outlet port 160. A separation device or system according to the present specification may include monitoring or sensor/analysis means 500 and/or separator or collector 400. For example, the sensor may provide countering of the size and numbers of particles passing through an observation point at different separation frequencies, or, countering may be provided for example at the end of a micro-magnet array.

Figure 4A:
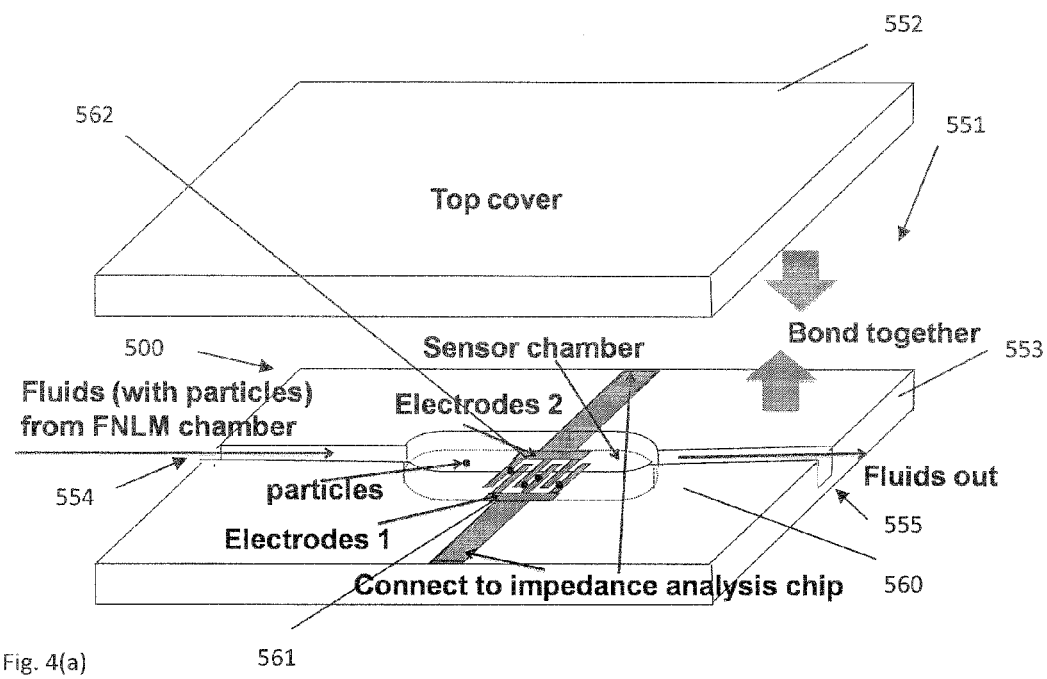
FIG. 4(a) is a schematic illustration showing a perspective view of an alternative sensor for use with the separation system according to the present specification.
Figure 4B:
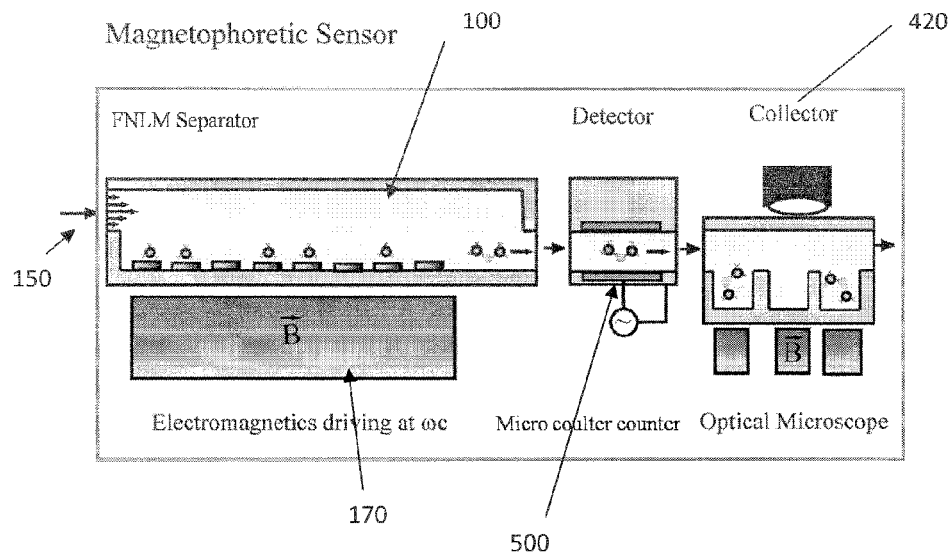
FIG. 4(b) is a schematic illustration showing a side view of a separation system of the present specification in use with a sensor of FIG. 4(a) and a collector of a further alternative system according to the present specification.

Referring to FIGS. 4(a) and 4(b) the separation system 100 may be used with a sensor 500 incorporated into a chip 551 having a substrate 552 and cover 553 and comprising an impedance sensor 560 including electrodes 561, 562 connected to an impedance analysis chip. The impedance measurement arrangement provides high resolution, enabling measurements for example of simple electrons, size exclusions. Here it is noted that the channel 554 which defines an inlet 554 to the impedance sensor is sized to control and provide a sorting of the cells as they pass through the channel for counting. This type of arrangement is suitable for use for example in cytometry for example counting stem cells in blood. The sensor arrangement allows for the detection of particles passing the electrode, recognition of particles for example based on size and counting. An outlet channel 555 is also provided for example to a collector.

Referring to FIG. 4(b) the separation system 100 is connected to sensor 500, for example, an impedance analysis sensor 560 or a micro-coulter counter for sensing and countering the particles, which have been separated. In a further alternative the arrangement may further included an integrated a linear magnetophoretic collector 420 provided downstream of the F-NLM separator and having a number of bins for collection of different bead or particles which have been separated by the F-NLM separation system. It will be appreciated that while the separation system, sensor and collector are shown in the exemplary FIG. 4(b) as being connected in series, in an alternative arrangement these components may be integrated into a single lab on chip arrangement.

Thus the system and method as described above and with reference to FIG. 1 and the other drawings may support a variety of sensing, analysis, and monitoring arrangements including for example, optical monitoring, magnetic monitoring, monitoring for fluorescently labeled marked for example, stem cell markers. Impedance measurements, and countering of particles, or measuring size of particles. The system may be operated in a diagnostic mode for identification or separation of for example analytes. The system may also be operated in a self-sorting mode. The system may be arranged to provide for a lining up of separated sample particles for counting or analysis.

While an exemplary system has been described initially with reference to FIG. 1, it will be appreciated that suitable alternative arrangements may also be provided. For example, in alternative arrangements a least one or multiple non-magnetic flow channels 140 may be used for separation. Similarly, at least one or multiple discrete magnetic arrays may be provided. Referring to FIGS. 5 and 6 further alternative arrangements of magnet arrays, non-magnetic channels and flow are shown. For example, in an alternative arrangement sheath flow may be used in a similar configuration. Furthermore, while flow has been described with reference to the exemplary arrangement of FIG. 1 as normal to the NLM (non-linear magnetophoretic) transport, it will be appreciated that the flow may alternatively be applied in an alternative direction for example, a substantially parallel direction to NLM movement by magnetic field. It will be appreciated that the magnetic means for providing the external magnetic field may be integrated into the chip assembly device as may other sensor/monitoring or collection/analysis components.

Figures 5A, 5B:
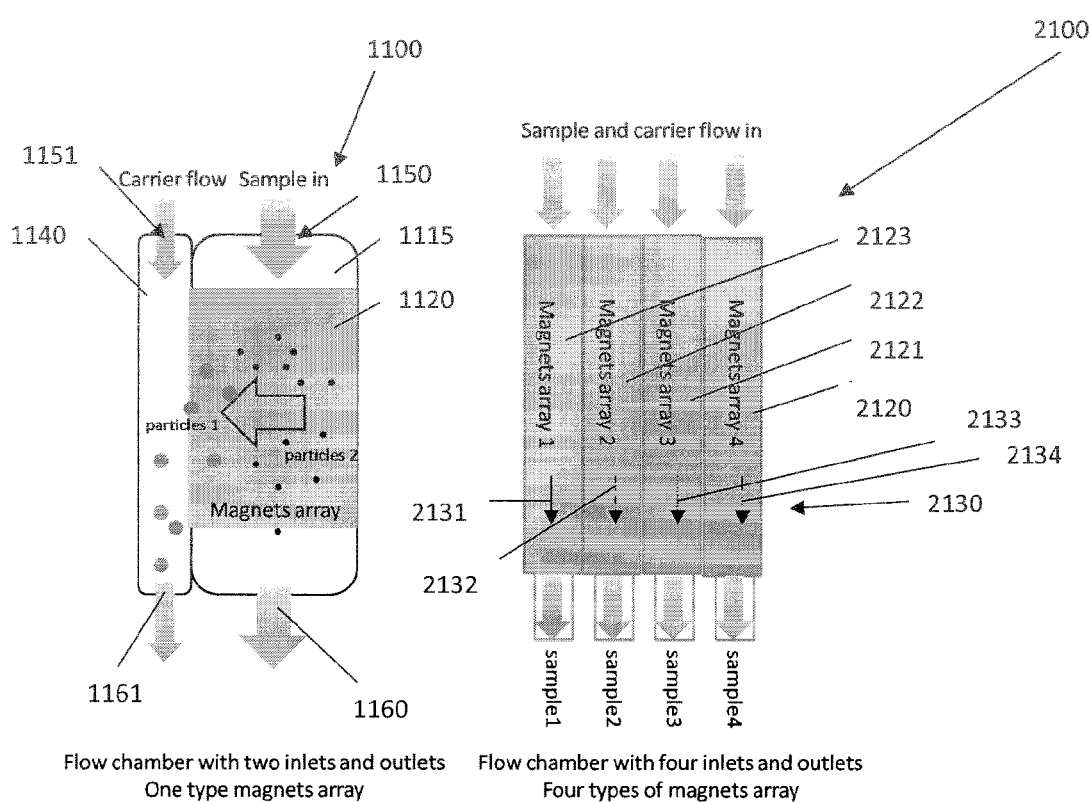
FIGS. 5(a) and 5(b) are schematic illustrations of alternative system and chip arrangements according to the present specification. In particular.

Referring to FIGS. 5a and 5b a number of exemplary alternative separation system, chip assembly and flow chamber, arrangements are described. The flow chamber of FIG. 1 has an inlet and outlet and first and second fluid paths, as described previously. Referring to FIGS. 5a and 5b, in exemplary arrangements shown, the flow chamber may comprise multiple inlets and outlets coupled to separate fluid paths. Referring to FIG. 5a, a system 1100 is provided including a magnetic array 1120 in a main channel or first fluid path 1115 and a second fluid path or by-pass channel 1140 provided located beside the main channel 1115. The system includes two inlets 1150 and 1151, inlet 1150 being provided to the first fluid path 1115 and the magnets array 1120 and inlet 1151 being provided to the second fluid path or by-pass channel 1140 respectively. The by-pass channel 1140 is similar to the non-magnetic channel 140 described previously, for example with reference to FIG. 1. The carrier flow in the by-pass channel 1140 may be configured such that once specific particles have been moved to the boundary of two channels 1140 and 1115, the carrier flow in the by-pass channel 1140 will sweep the beads/particles downstream in the direction of flow to the outlet means 1160. In the case of a sample having first and second type particles/beads, the beads/particles of the second type may accordingly be separated via a first outlet provided on the by-pass channel 1161 and beads/particles of the first type may be separated via another outlet 1162. In contrast to the FIG. 1 arrangement, preferably the flow rate in two channels 1140 and 1115 may be adjusted separately and independently of each other. The flow rate and resultant velocity down the side of the magnet-array in the by-pass channel may be adjusted to provide a different velocity for example, to provide more efficient separation. This arrangement provides for additional control in the separation and advantageously provides a reduction in the time required for a separation. The arrangement advantageously provides for the continuous introduction of a sample and separation.

Referring to FIG. 5b a further exemplary arrangement is shown in which multiple magnet arrays, each having different properties in this case each with different periodic characteristics, are arranged next to each other in a flow chamber 2130 having multiple inlets and outlets to first, second, third and fourth fluid paths (2131, 2132, 2133, 2134) or channels respectively. The arrangement provides for the simultaneous separation of multiple sample constituents or analytes. In such an arrangement, the different magnet arrays 2120, 2121, 2122 and 2123 are configured to separate different particles simultaneously at the same separation frequency, due to the different periodic parameters of each of the respective magnetic arrays. The different magnet arrays 2120, 2121, 2122 and 2123 are provided in this exemplary arrangement in or proximal the different fluid paths, namely first to fourth fluid paths respectively. As described with reference to FIG. 1 the magnetic arrays may comprise multiple sub-magnet arrays with non-magnetic flow channels arranged therebetween. The arrangement of FIG. 5b may advantageously be used to separate multiple particles simultaneously at the same operable frequency of external magnetic field with a relatively fast separation time. The exemplary system 2100 comprises four inlets and four outlets, four fluid paths and four different types of magnetic arrays and as shown the four sample types are outputted at the outlets. The system provides for the control of the rate of flow on each of the magnet arrays as required.

Figures 6A, 6B, 6C, 6D:
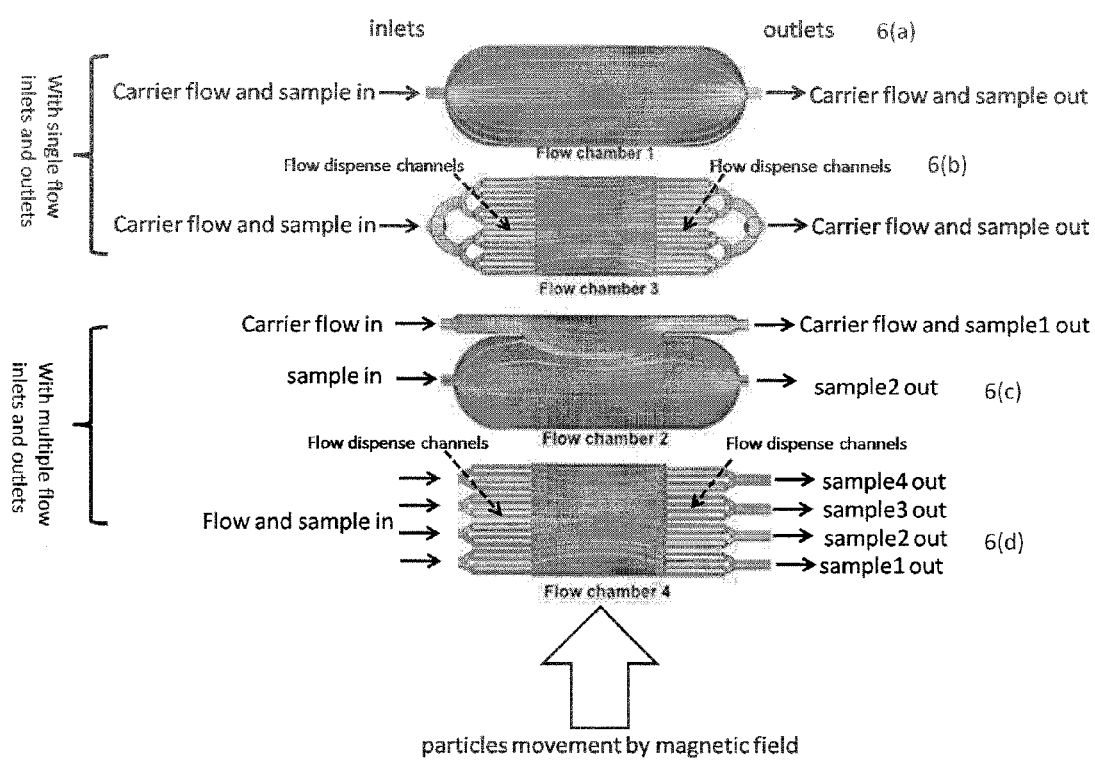
FIGS. 6(a) to 6(d) (from top to bottom) are schematic illustrations from above of four alternative system and chip and flow chamber arrangements with Finite Element Modeling of flow profile in the chambers, according to the present specification illustrating also various configuration of inlets and outlets and flow managements features.
Figure 6:
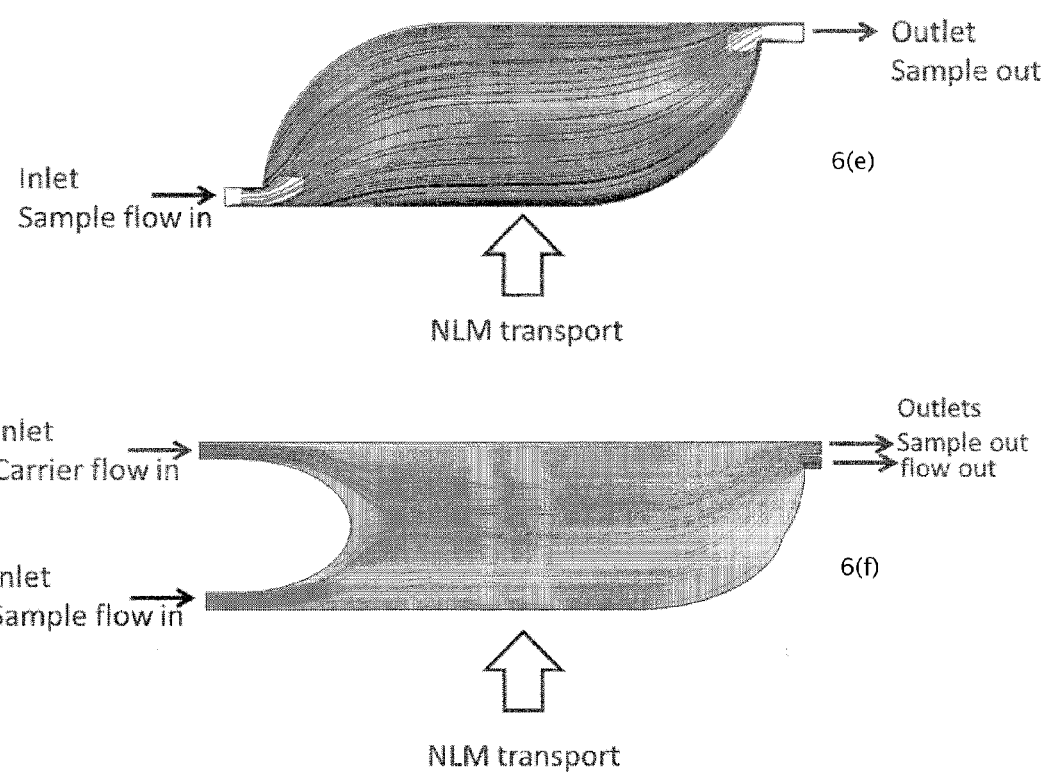
FIGS. 6e and 6f show examples of asymmetric flow arrangements with FIG. 6a showing a single inlet and outlet and FIG. 6b showing a dual inlet and a single outlet arrangement.

FIGS. 6(a) to 6(d) are schematic illustrations of the layout of different alternative systems, device assemblies and flow chamber arrangements according to the teaching of the present specification as described above with reference to FIGS. 1 and 5. Flow is shown to be between the inlets and outlets and the direction of transport by the external rotating magnetic field is shown to be normal to the direction of flow. Referring to FIG. 6(a) a separation system and chip having a single inlet and outlet are shown. This arrangement is similar to that of FIG. 1.

Referring to FIG. 6(b), a different flow is provided by the use of flow dispensing channels between the inlet and fluid paths magnetic array/s and separation non-magnetic channels and the outlet. The system comprises a plurality of fluid paths. The flow dispensing channels advantageously provide a more uniform flow than may be achievable with a single inlet, hence avoiding effects that may sometimes arise where there may be variation in flow between channel sides and centre for example. As described with reference to specific examples later, depending on the type of separation required different optimal flow rates via the device and system apply.

Referring to FIG. 6(c) an arrangement similar to that described above with reference to FIG. 5(a) is illustrated. Two inlets and outlets are provided. An inlet and outlet is provided to each of the second fluid path or by-pass channel being the non-magnetic channel and to the main channel or first fluid path including the magnetic arrays. This arrangement preferably provides for independent control of the flow rates on the second and first fluid paths and on non-magnetic channel and the magnet array. Advantageously, the arrangement provides that separation may be operated continuously and not sequentially. The separation of particles or beads of a first and second type is illustrated. Micro-beads of the first type are separated from the micro-beads of the second type on the micro-magnet array as described above. The micro-beads of the first type are then moved from the edge of the micro-magnet array by carrier flow in the non-magnetic channel to the first outlet.

By combining with an external magnetic field, the micro-magnet array 120 can be used as a magnetic particles collector to capture the particles, which have been introduced into the flow chamber 130, on the magnets array surface before applying the rotating magnetic field. This separation and capturing of particles can be performed simultaneously and continuously. In another configuration separation may be performed after the particles are collected on the micro-magnets array 120 by introducing the carrier fluid into the flow chamber 130 and then pausing for a pre-determined time period, for example one minute, to allow the magnetic beads to be collected on the micro-magnet array with the z-direction electromagnet. Simultaneous separation and capture can give more efficient capturing of particles on the micro-magnet array.

Referring to FIG. 6(d) a system and chip are shown having multiple inlets, and multiple outlets. In addition flow dispensing channels and provided between the inlets and outlets and different fluid paths comprising the separation magnetic arrays/non-magnetic channels. This arrangement advantageously provides for and supports multiple separations on a single chip.

In other configurations asymmetric flow chambers may be used for F-NLM. In scenarios where the flow direction is opposite to the NLM transport of the particles it is difficult to control the transport of particles. Such scenarios may arise near the outlet of a single inlet, single outlet arrangement such as shown in FIG. 6a. To avoid the generation of an opposite flow on the magnet array area, the flow chambers may be designed to be long enough to keep the magnet array located in the center of flow chamber, so the flow profile on magnet array area will have no opposite flow. In another configuration such as shown in FIGS. 6(e) and 6(f) asymmetric flow chambers may be employed to reduce the length of flow chamber and avoid the opposite flow. In simulation of asymmetric flow chambers, the NLM transport of magnetic particles is always perpendicular or in same direction with flow direction. FIG. 6e shows a first type of asymmetric flow chamber having a single inlet and outlet whereas FIG. 6f provides two inlets and two outlets.

While in the various arrangements of system and method described with reference to the present specification, separation or transport of micro-beads/particles of the second type in the non-magnetic separation channel has been provided using flow and by control of the rate of flow and the hydrodynamic forces, it will be appreciated that suitable alternatives to flow may be provided for example, by application and provision of electro-kinetic forces or gravitational forces or centrifugal forces.

As described above, the arrangement of the present specification provides for first and second fluid paths and transport of particles of a second type to a second fluid path. Means is provided for applying a force to particles of the second type in the second fluid path to affect their transport and separation. In the exemplary arrangement described above the force may be flow. However, it will be appreciated that suitable alternative forces may be applied as noted above.

The exemplary system and device arrangements for example as described with reference to FIGS. 1 to 6, support a method of non-linear magnetophoretic separation to provide separation of first and second particle/bead types of a sample which includes the following:

Providing a separation system/device comprising a magnet array in a first fluid path and a non-magnetic separation channel in a second fluid paths, Introducing a sample comprising first and micro-beads of the second type into the system, Applying a rotating magnetic field proximate to the magnet array, Controlling the frequency of the rotating magnetic field, and the flow rate to provide separation of said micro-beads of the second type from said micro-beads of the first type.

The method provides a flow enhanced non-linear magnetophoretic separation (F-NLM).

Flow in first and second fluid paths is controllable as required. The external magnetic field is operable at a frequency of rotation above the critical frequency of the micro-beads of the first type and below a threshold frequency of micro-beads of the second type to effect a separation thereof affecting the trapping of the micro-beads of the first type on the magnet array and transport of second-micro beads across the magnet array to the non-magnetic separation channel adjacent an edge of the magnet array.

A non-magnetic force is applied to transport micro-beads of the second type downstream from said edge of the magnet array to effect separation of said micro-beads of the second type. The non-magnetic force may be flow, wherein the method includes applying flow and controlling the rate of flow such that the resultant hydrodynamic forces affect transport and separation of said micro-beads of the second type. The rate of flow is controllable such that the induced hydrodynamic force is in a range less than the force needed to displace the micro-beads of the first type trapped on the magnet array and greater than that need to displace micro-beads of the second type which have been transported to the edge of the magnet array. The force, for example flow in the second fluid path or non-magnetic channel may provide transport of the micro-beads of the second type or particles to a collector. Similarly, after the micro-beads of the second type have been separated from the micro-beads of the first type and transported downstream by flow, the frequency of rotation of the external magnetic field is reduced to a frequency below the critical frequency of the micro-beads of the first type to effect transport by non-linear magnetophoresis of the micro-beads of the first type to the edge of the micro-magnet array and transport of the micro-beads of the first type from said edge of the micro-magnet array downstream. Alternatively, after micro-beads of the second type have been separated the rate of flow may be controlled such that the induced hydrodynamic force in the magnet array is sufficient to displace and transport said micro-beads of the first type that have been trapped on the magnet array downstream. A collector may also be provided for receiving micro-beads of the first type. The method may further include collecting or counting or analysing said first and micro-beads of the second type that have been separated. The frequency of rotation and flow rate may be controlled to provide a continuous separation.

Example results and data from an example separation using an exemplary separation device 100 are provided with reference to FIGS. 2 and 3 and also FIGS. 4, 5, 6, 7, 8 and 9 based on the use of the system 100 of the present specification to isolate *B. globigii* and *S. cerevisiae* captured on 1.0 and 2.7 micron diameter magnetic beads functionalized with specific antibodies by fixing ω at a value that would trap the beads bound to the microorganisms on the array.

Example

In an exemplary arrangement, an embodiment of a separation system 100 was provided comprised of an array of micro-magnets embedded in a flow chamber with fluidic ports. A double-layer, negative resist photolithographic lift-off process was used to fabricate the cobalt micro-magnets with a high degree of dimensional control. The micro-magnet array was composed 5.0±0.1 μm diameter circular magnets arranged in a square lattice with 8.0±0.1 μm center-to-center distance. The micro-magnets were created by thermally depositing 5 nm chrome, 70 nm cobalt, and 5 nm chrome on the developed photoresist. After the removal of the resist the resulting micro-magnets were inspected with scanning electron microscopy (SEM) and atomic force microscopy to determine their z and xy dimensions with 1 and 10 nm resolution, respectively. The micro-magnet arrays were coated with a substantially 600 nm thick spin on-glass (SOG) layer (Filmtronics, Butler, Pa., USA) to provide chemical protection. The rectangular flow chamber around the magnets array was formed using a SU-8 (MicroChem, Newton, Mass., USA) photolithographic process. The rectangular flow channel was of dimensions of the order of 47 mm long, 7.8 mm wide, and 70 μm high. The microfluidics chamber was completed by using laser machining to form inlet and outlet holes substantially of dimensions of 1 mm diameter and then bonding a 170 micron thick quartz sheet to the SU-8 layer to from a closed chamber. The form of the flow chamber was configured to allow the velocity of fluid flow to be set with 10% precision down the length of the chamber and the motion of the particles on the arrays to be characterized with an optical microscope.

A rotating magnetic field orthogonal to the axis of flow on the chip was provided generated with three electromagnets 170 comprised solenoids of 570 coils surrounding a cylindrical iron core of diameter of 60 mm and length of 150 mm were provided. Two synchronized sinusoidal signals with a 90 degree phase difference were generated with a controller 161 comprising two-channel function generator (Tektronix, Beaverton, Oreg., USA). This signal was amplified to the desired current using two programmable amplifiers (Kepco, Flushing, N.Y., USA) and supplied to the electromagnets assembled on the x and z axes. This generated an elliptical, rotating magnetic field with an amplitude of 48 and 29 Gauss in the z-direction and x-directions, respectively. The uniformity of magnetic field generated by the electromagnets was >96% in the axial direction and >83% in the radial direction.

The separation was performed after the particles were collected on the micro-magnet array 120 by introducing the carrier fluid into the flow chamber 130 and then pausing for one minute to allow the magnetic beads to be collected on the micro-magnet array with the z-direction electromagnet.

Off-chip fluidic handling was used to control the flow on-chip and collect magnetic bead fractions. The syringe pumps (Chemyx, Stafford, Tex. USA) were used to introduce sample and rinse fluids at specified flow rates between 20 and 300 microliters/minute.

The Reynolds number (Nre) for a rectangular channel is $$N_{re} = \frac{\rho V_o D_h}{\mu},$$

where $V_o$ is the average velocity of the liquid, $D_h$ is the hydrodynamic diameter of the channel, and $\rho$ and $\mu$ are the density and viscosity of the fluid, respectively. In an exemplary arrangement an $N_{re}$ of the order of magnitude of $10^{-7}$ for non-linear magnetophoretic transport under continuous flow (F-NLM), which is deep in the creeping flow regime.

F-NLM separation was executed after the beads were collected on the micro-magnet array by introducing the carrier fluid into the chamber at a defined flow rate and activating the rotating magnetic field at a specific frequency. Sample fractions separated at specific frequencies were collected using a valve manifold on the outlet port.

The transport properties of the F-NLM device were characterized with an epi-illumination, optical microscope (Zeiss Axioskop 2, Welwyn Garden City, UK) with a 63× long-working distance 80 lens. Images of the magnetic beads on the micro-magnet array were acquired with a high-speed camera (Axiocam Hsm, Zeiss) capable of resolving the 1 μm diameter beads in a 140×110 μm field of view with 10 ms resolution.

Reagents

Two different super-paramagnetic particles were used in this study, i.e., carboxyl coated My-one and M-270 particles were purchased from Invitrogen (Carlsbad, Calif., USA). The diameter of the particles were measured with scanning electron microscopy (Hitachi S-4300) to be 1.0 and 2.8 μm, respectively, and coefficient of variation (CV) of the diameter of each particle was less than 3%. The magnetic properties of particles was measured with SQUID magnetometry (type). These measurements were conducted at room temperature by dispersing the particles on a silicon substrate. The saturation magnetization of the particles was found to be 300 kA/m at 0.2 T. The magnetic susceptibility ($\chi$) of the 1.0 and 2.8 μm particles was 0.3 and 0.17, respectively. The particles were dispensed in a 1 mM phosphate buffered saline solution with 0.5% Triton X-100 solution (PBST). The PBT solution was also used as the carrier fluid.

Transport

Figures 7A, 7B, 7C:
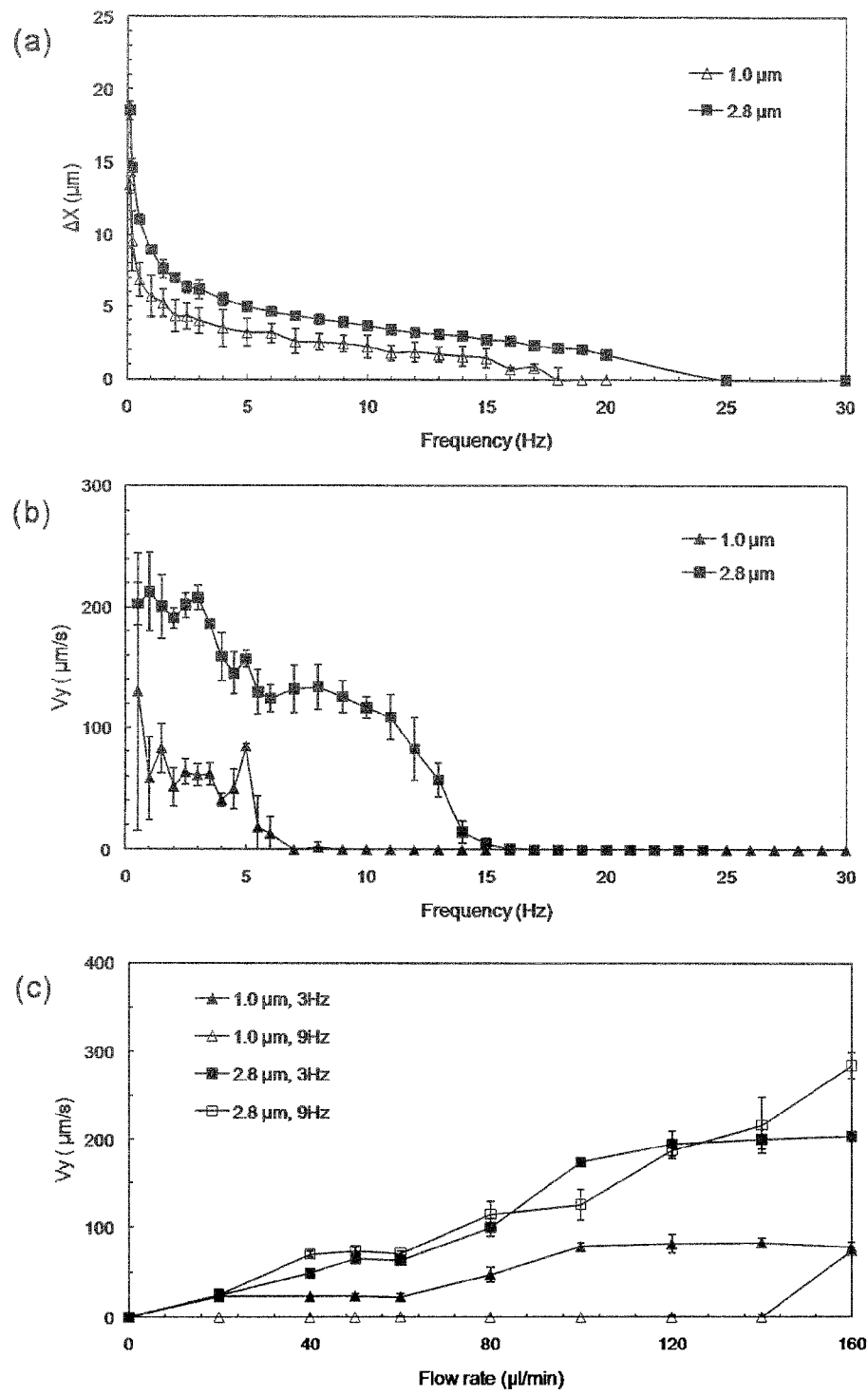
FIG. 7A is a graph illustrating amplitude of oscillation of the particles on the edge of the micro-magnetic array as a function of frequency of rotation of the magnetic field without flow.
FIG. 7B. is an graph illustrating speed of particle motion in the direction of flow at the edge of the micro-magnet arrays as a function of frequency of rotation of the magnetic field in a fluid flowing at 100 μm/min.
FIG. 7C is a graph showing the speed of 1.0 and 2.8 micron particles on the edge of the magnetic array as a function of flow rate and frequency of rotation of the magnetic field.

Referring to FIGS. 7(a), 7(b) and 7(c), the motion of magnetic beads on the continuous micro-magnet arrays was studied as a function bead size (d), external magnetic field rotation frequency (ω), and flow rate (q) with an optical microscope. In the absence of flow the beads were observed to move across the micro-magnet arrays at low frequencies but became immobilized at a characteristic frequency. The critical frequency, $\omega_c$, of the beads was determined at which the average bead velocity, $V_x$, diverged from the velocity of the translating potential energy landscape. The velocity of the 1 and 2.8 μm diameter beads was measured as a function of the external magnetic field rotation frequency and $\omega_c$ was found to be 4.5 and 9 Hz, respectively. The frequency at which half of the 1 and 2.8 μm diameter magnetic beads were immobilized on the micro-magnet array, which we will define as the threshold frequency $\omega_t$, was found to be 5.5 and 12 Hz, respectively. The variation in transport behaviour of each lot of beads was observed in the magnitude of ($\omega_t - \omega_c$) and is likely to result from variation in bead magnetization, which has been shown to vary by as much as 25% within a given sample of beads. The motion of the beads on the continuous micro-magnet array was also studied as a function of fluid flow rate. At flow rates less than 140 μl/min very little change in NLM transport behaviour could be detected. At flow rates greater than 140 μl/min the 2.8 μm beads were observed to start to become displaced from the micro-magnet array and move down the microfluidic channel in the direction of flow. The 1.0 μm beads began to become displaced from the micro-magnet array at a flow rate of 180 μl/min and were also observed to move with the flow. Both magnetic beads were observed to become displaced from the micro-magnet array over a wide distribution of flow rates.

Transport behaviour of the magnetic beads on the continuous micro-magnet arrays The motion of the magnetic beads on edge of the micro-magnet arrays was also studied as a function of d, ω, and q. The beads on the edge of the array were found to oscillate between the edge of the micro-magnet and a position in the flow channel, as illustrated in FIG. 3. FIG. 7(a) presents the measured amplitude of this oscillation, ΔX, as a function of ω at q=0, where ΔX is defined as is the distance from the centre of bead when beads reach its maximum distance from the micro magnet to the edge of the micro-magnet. Referring to FIG. 7(a) it is noted that, ΔX was found to decrease as ω increased. This decrease was found to take place at two rates. At ω<1 Hz the ΔX was found to decrease rapidly while at ω>1 Hz ΔX decreased less rapidly. Second, the smaller beads had a smaller ΔX across the range of frequencies for which displacement was measured. Third, there is a threshold frequency at which ΔX becomes zero, which we define as the point where the bead sticks to the surface of magnet and oscillates at its point of contact. This threshold frequency was between 15-20 Hz and was significantly larger than $\omega_t$ of both beads.

FIG. 7(b) presents the velocity of the beads measured moving along the edge of the micro-magnet array in flow, $V_y$, as a function of ω at a flow rate of 100 μl/min. It is noted first, that that at ω less than a threshold frequency, $\Omega_t$, the beads at the edge of an array will move with flow. Second, at ω>$\Omega_t$ the beads stop moving in the direction of flow. The magnitude of $\Omega_t$ was quite close to $\omega_t$ for the 1 μm beads but was 15 Hz for the 2.8 μm beads. Third, $\Omega_t$ and $V_y$ were a function of the physical properties of the beads with the larger beads exhibiting higher values of $\Omega_t$ and $V_y$.

FIG. 7(c) summarizes the measurement of Vy of the beads as a function of flow rate at two frequencies of rotation of the external magnetic field. These results illustrate that $V_y$ is a function of q, ω, and d. Four trends can be drawn from these results. First, larger beads moved faster than the smaller beads. Second, Vy for the larger beads appears to be independent of ω. Third, the small beads were confined on the edge of the micro-magnet array at 9 Hz. Fourth, at higher flow rates, i.e., q>160 µl/min, all the beads on the edge of the array were swept away into the flow channel. It appears that the optimum range of flow rate for separation are in the range of 100 µl/min.

Referring to FIGS. 8A to H, separation of the magnetic micro-beads using F-NLM is further shown in an example in which separation is demonstrated by stepping to frequency of rotation ω of the external magnetic field through a series of frequencies at a flow rate of 100 µl/min.

Figure 8:
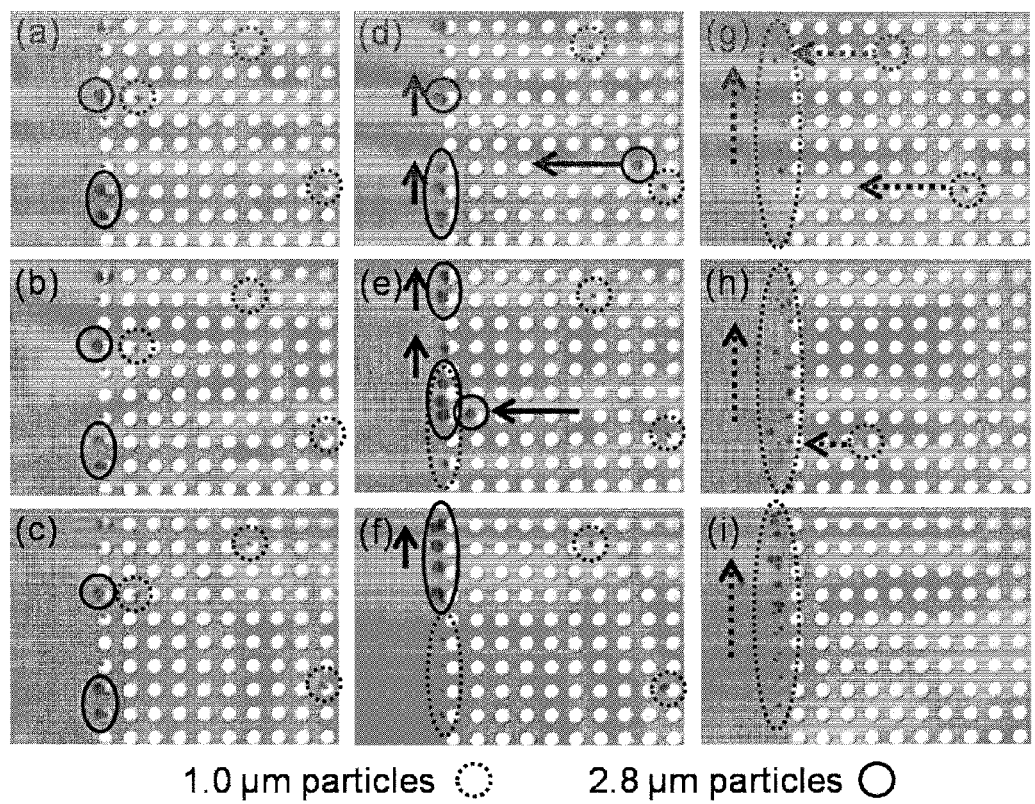
FIGS. 8A to 8G are micrographs showing micro-particles on the edge of a micro-magnet array at different separation frequencies of rotation of the magnetic field and flow Vo=100 μm/min.

FIG. 8 illustrates an exemplary separation provided in three steps. Initially, the external field frequency was set at 30 Hz, which exceeds the critical frequency of all the particles. FIGS. 8A, B, and C show that the particles were fixed on the micro-magnet array. In the second step, the field frequency was increased to 9 Hz where $\omega<\omega_{c,\ 2.8\ \mu m}$ $<\Omega_{c,2.8\ \mu m}$ and $\omega>\omega_{c,1\ \mu m}$. FIGS. 8D, E, and F show the smaller 1 µm particles fixed on the array while the larger beads move across the array until they encounter an edge where they follow the direction of flow. In this way, the large beads were separated from the micro-magnet array 120 in the flow direction while the 1 µm particles were trapped on the micro-magnet array 120. In the last step the frequency was decreased to 3 Hz where $\omega<\omega_{c,1\ \mu m}$ and $\Omega_{tc,\ 1\ \mu m}$. FIGS. 8G, H, and I illustrate that the small particles were displaced from the chip and separated in the laminar flow.

The exemplary F-NLM (flow enhanced non-linear magnetophoresis) separation illustrated shows that the separation using the separation device 100 provides a separation of multiple magnetic particles at different frequencies. The last remaining particles on the magnetic array were displaced by increasing the laminar flow to sweep the remaining particles downstream.

Analysis of Motion of the Particles on the Micro-Magnet Array

The magnetic force generated on a bead by a rotating magnetic field on a micro-magnet array has been previously described as $$F_x(x,t) = F_{mag} \sin(kx - \omega t) \qquad \text{eq 1}$$

where $F_{mag}$ is the maximum magnetic force and $k=2\pi/d$ is a constant describing the spatial periodicity of the array. The solution of the equation of motion for this bead reveals the bead's motion can be described as an overdamped non-linear oscillator. The critical frequency for this oscillator is $$\omega_c = \frac{\overline{\chi}\mu_o \sigma_o H_{ext}}{18\eta}(2\pi\beta)^2 \exp(-2\pi\beta) \qquad \text{eq 2}$$

where, $\mu_0$ is the permittivity of space, $\sigma_o$ is an experimentally determined parameter representing the effective magnetic pole distribution on the array surface, η is the drag coefficient, $H_{ext}$ is the magnitude of the external magnetic field, and β is the ratio of the bead radius, a, to the characteristic length scale of the array, b.

Overdamped non-linear oscillators are dynamic systems exhibiting two distinct transport regimes depending on the magnitude of the external driving frequency. When the external driving frequency is less than a critical threshold, the bead reaches a stable position within a given trap in the landscape and moves at a constant horizontal velocity with a speed equal to the translation velocity of the landscape, ωd/2π. Near the critical threshold, the bead will lag behind the local energy minima. Above the critical threshold, the beads begin to slip with respect to the translating potential energy landscape. Physically, this slipping is observed as an oscillatory rocking motion between adjacent magnets superimposed on a time-averaged linear velocity, which reduces to zero with increasing frequency at a rate defined $(\omega-\sqrt{(\omega^2-\omega^2_c)})/d/2\pi$.

Analysis of magnetic field at the edge of the micro-magnet array and motion of the magnetic beads.

Figure 2B:
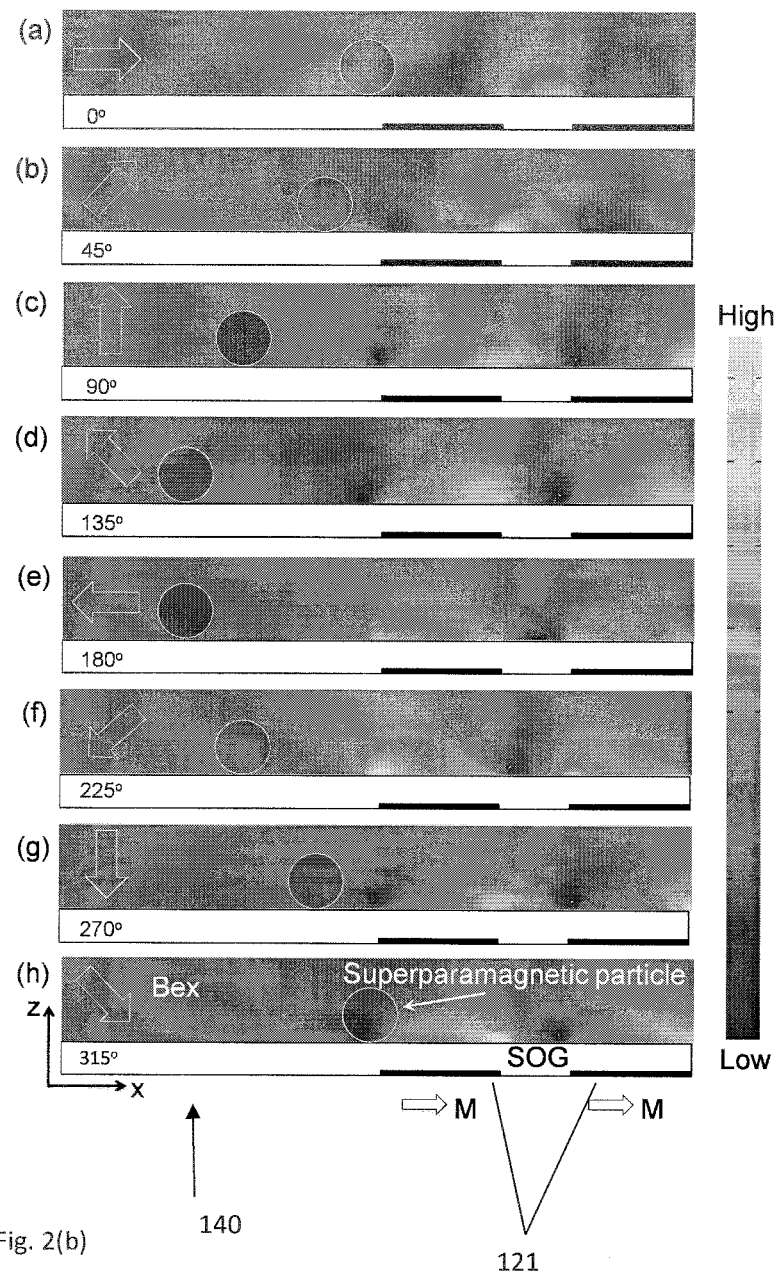

The magnetic field distribution at edge of a micro-magnet array was calculated using finite element modeling. FIG. 2b presents cross-sectional images of the normalized magnetic flux density, $$B = \sqrt{\vec{B} \cdot \vec{B}}$$

in an xz-plane that insects the centre of two micro-magnets (FIG. 3) as a function of the orientation of the external magnetic field, θ. The magnitude of the B has been presented in light/dark colour with a single scale used for all eight images. The magnetic potential energy of the super-paramagnetic beads will cause the beads to move towards the maximum B, i.e., the magnetic force Fm drives the bead to maximum B $$\vec{F}_m = (m \cdot \vec{\nabla})\vec{B} = V \cdot \frac{3 \cdot \chi}{\chi + 3} \nabla \frac{B^2}{2\mu_o}. \qquad \text{Equation (3)}$$

To guide the eye the equilibrium position of magnetic bead has been drawn onto these calculations at the point of estimated maximum B. Observations are drawn from the series of B cross-section calculations in FIG. 2b that provide details of the motion of the magnetic beads at the edge of the micro-magnet array. First, the B distributions on both the inner and outer micro-magnets have a similar form in most orientations of the external magnetic field. For example, B is high just to the right of the micro-magnets when θ is 135° and is low on the left side of the micro-magnets as θ rotates to 45° Second, B in the flow channel beside the micromagnets is constant at 60 Gauss, which is equal to the field intensity produced by the electromagnets. This B is significantly lower than the maximum B on the micro-magnetic array. Third, B in the channel was higher than B on the left side the outer micro-magnet at θ between 90° and 180°. These calculations suggest that once a magnetic bead travels to the edge of the micro-magnet array it is captured in a local magnetic field that oscillates between a point on the edge of the micro-magnet and a point in the channel. This motion of the B has similarities to the motion of B on the continuous micro-magnet array with the noted exception that it returns to the same micro-magnet. It also appears that the beads trapped on the edge of the micro-magnet array were not captured in a local B maximum between 90° and 225°, but to move in a relatively uniform B. These fields produce low magnetic forces that allow the beads to move down the edge of the micro-magnet array due to hydrodynamic drag when the external field angle is 90°<θ<225°.

Figures 9A, 9B, 9C:
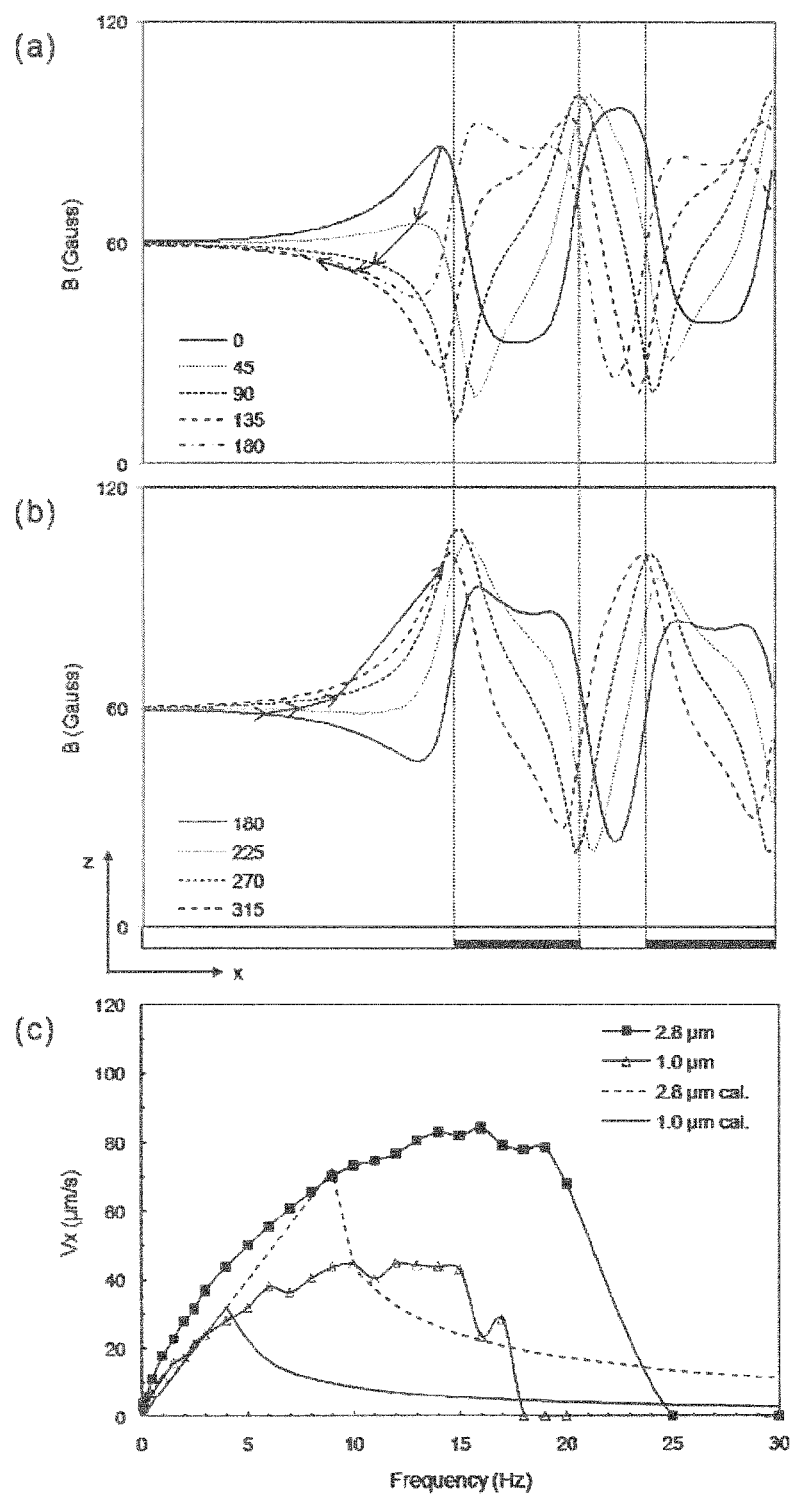
FIGS. 9A and 9B are graphs showing the amplitude of the magnetic field 0.5 micron-meter above surface of substrate, which is the location of 1 micron particles, at the edge of the micro-magnet array as a function of the orientation of external magnetic field.
FIG. 9C is a graph showing Velocity of the particles in the x-direction, Vx, as a function of external magnetic field frequency of rotation ω.

An analysis of the B field was also done in three dimensions for a 5*3 micro-magnet array. The results were found to be consistent with the results of the analysis in 2-dimensions FIGS. 9(a) and 9(b) present B as a function of θ in an xz-plane along the centre of the two micro-magnets 0.5 µm above the SOG surface (FIG. 3, line 1). As mentioned above the bead will 30 move along the x-axis to the region of maximum local B. Clearly, B does not have a simple functional form thus the equation of motion of the bead cannot be solved analytically as was the case in NLM. FIG. 9(a) presents B as θ rotates from 0 to 180° resulting in the displacement of the bead from the left side of the outer micro-magnet into the flow channel.

FIG. 9(b) shows the magnetic field (B) that results in the displacement of the bead from the flow channel back onto the outer micro-magnet as θ rotates from 180 to 315°. Arrows have been drawn on each of these figures to illustrate a solution for the position of the bead as θ increase. Several observations can be made about the B field generated at the edge of the micromagnet array from these calculations. First, unlike NLM it is clear that the bead does not always move in a local B maximum. Rather, it starts in a B maximum at the left edge of the outer micro-magnet at θ=0°. At θ=90° there no longer is a maximum B, but the bead moves up the B gradient into the channel until θ=180° where the bead reverses its direction as it moves toward the B maximum that has been created at the side of the outer micro-magnet. Second, B on the left edge of the micro-magnet adjacent to the channel exceeds that on the inner micro-magnet for θ between 180 and 315°. This B serves to retrieve the bead from the channel in flow and to hold the bead in place.

FIG. 9(c) presents $V_x$ of the 1.0 and 2.8 μm beads calculated from the ΔX vs. ω data in FIG. 7(a). The velocity of the beads increased until θ reached $θ_c$ after which the velocity stabilized until ω reached a threshold frequency which was 17 and 21 Hz for the 1 and 2.8 μm beads, respectively. The trends observed in FIG. 9(c) have some similarities to those observed in NLM, i.e., the velocity of the beads increases until the frequency reaches $ω_c$. However, at frequencies above $ω_c$ the velocity does not decrease but remains constant until a threshold frequency is reached. This appears to result from the fact that the B in the channel next to the micro-magnet array does not have a maximum for 90°<θ<225° but increased monotonically toward the B in the channel produced by the electromagnet. The result is that $V_x$ does not decrease at higher frequencies but rather remains approximately constant until ω is greater than the threshold frequency at which point the bead does not appear to have sufficient time to move into the channel. The $V_y$ of the magnetic beads as a function of ω was presented in FIG. 7(c). Analysis of B generated the micro-magnets in FIGS. 9(a) and (b) suggests that $V_y$ should not depend on frequency for $ω<Ω_t$ and this was in fact observed in the results presented in FIG. 7(c). That is, at frequencies less than $Ω_t$ the velocity of the 1 and 2.8 μm bead was approximately 60 and 180 μm/s, respectively, for flow rates of 100 μl/min. It appears that the velocity of the 1 and 2.8 μm beads at the edge of the array was proportional to the size of the bead at a given flow rate despite the fact that the velocity of the fluid at the surface of the flow chamber was a non-linear function of z, and magnetic force (Equation 3) is complex function of the bead physical properties and magnetic field.

In the exemplary system and method described heretofore, the transport of super-paramagnetic beads on a micromagnet array has been studied in a hydrodynamic flow field. It has been observed that flow has little influence on the magnetically activated transport of the beads moving on a continuous micro-magnetic array until the velocity was increased to a level that swept the beads away from the array. It can also be concluded that flow has a more controlled influence on the motion of beads trapped at the edge of a micro-magnetic array. At ω greater than a threshold frequency, $Ω_t$, the beads were immobilized at the edge of the micro-magnet array. At $ω<Ω_t$ the beads moved along the edge of the micromagnet array at a velocity that was proportional to velocity and the radius of the bead.

Insight into this behaviour was gained from finite element calculations of the magnetic flux density, B, produced by the micro-magnet at the edge of the array as a function of external magnetic field orientation, θ. The B profile took on two forms as θ increased from 0 to 360°. As θ increased from 0 to 180° the bead traveled from a local magnetic field maxima on the edge of the outer micromagnet into the flow channel where B was weak and lacked a local maximum. As θ increased from 180 to 360° the bead moves back to the edge of the micromagnet where a strong B maxima developed. These calculations provided insight into the forces that led to the capture the magnetic bead at the edge of the micro-magnet array and caused it to oscillate between a point on the edge of the micromagnet and a point in the channel. They also provide a basis for understanding why the threshold frequency on the edge of the micro-magnet array, $Ω_t$, is different from the threshold frequency on the continuous array, $ω_t$. It was striking note that both $Ω_t$ and Vy appear to scale with bead size for $ω<Ω_t$ at a flow rate of 100 μl/min. This suggests that $Ω_t$ and $V_y$ were dominated by hydrodynamic drag force, which is proportional to bead diameter.

Example for preparing the complexes of particles for separation of analytes in an example separation according the present specification:

Complexes of magnetic-fluorescent particles, were modified with polyethylene glycol (PEG) to minimize the non-specific adsorption between particles and analytes, are prepared for separation. Attached fluorescent particle will allow the separation process and results can be observed with ease using fluorescent microscopy. The complexes were functionalized with monoclonal antibodies against specific analytes (such as Dengue virus) for analytes separation and detection.

An example process for preparing this type of complex is as follows:

1. Modification and Functionalization of Particles

The surfaces of the paramagnetic particles was modified with carboxyl groups that were readily available for covalent coupling of proteins and other molecules. Magnetic particles were functionalized with the anti-dengue antibody by covalent bond attachment through a PEG monolayer, as described previously. The particles were first coated with a monolayer of primary amines by physically adsorbing polyethylene imine (PEI, Polymin SNA, BASF, Rensseler, N.Y., USA) on the negatively charged particles. These surfaces were then functionalized with a vinyl-sulfone PEG monolayer by reacting α-vinyl sulfone, Ω-N-hydroxysuccinimidyl ester of poly(ethylene glycol)-propionic acid (NHS-PEG-VS) (Nektar, Huntsville, Ala., USA) with the PEI coated particles. The antibody was modified with sulfhydryl groups using N-succinimidyl-5-acetylthioacetate (SATA, Pierce Biotechnology, Rockford, Ill., USA) at 1:10 ratio in 100 mM phosphate buffer, 150 mM NaCl, and 10 mM EDTA at pH 7.2. The sulfhydryl group was activated with a deacetylation buffer of 50 mM hydroxylamine-HCl, 2.5 mM EDTA, 62.5 mM $Na_2HPO_4$—$NaH_2PO_4$ at pH 7.5 for 2 h. The buffer was replaced on an excellulose desalting column (Pierce, Rockford, Ill., USA) with 50 mM $Na_2HPO_4$—$NaH_2PO_4$, 1 mM EDTA, pH 7.2. Approximately $10^{10}$ PEG-VS particles were reacted with 700 μg of the SATA activated antibody in desalting buffer. The 1±0.1 μm green fluorescent microparticles (Duke Scientific, Palo Alto, Calif., USA) were modified with anti-dengue antibody by following the same procedure.

2. Formation of Complexes

The magnetic and fluorescent microparticles were reacted at a concentration of approximately $10^4$ particles per ml, with killed type 2 dengue virus at a concentration of $1\text{-}10^4$ PFU $m^{-1}$ (plaque forming unit). These particles were functionalized with monoclonal antibodies against type 2 dengue virus using a polyethylene glycol (PEG) chemistry that minimizes the non-specific adsorption of proteins from the sample. The product of this reaction was a mixture of a large number of individual particles and a smaller number of magnetic-fluorescent, magnetic-magnetic, and fluorescent-fluorescent particles assembled through an antibody-virus-antibody bond. Then the magnetic particles were concentrated from the sample using a single step magnetic separation to allow the unbound fluorescent particles to be rapidly and efficiently separated from those bound to magnetic particles. After that, fluorescent-magnetic particle complexes could be sorted and be used as separation complexes for FNLM separation using a device or system according to the present specification for analytes detection.

It will be appreciated that this exemplary methodology of preparing complexes is provided to assist the person of skill in understanding how such complexes may be provided and is not intended to limit the present teaching to such a specific exemplary methodology. Fluorescent-magnetic particle complexes, once fabricated using any one of a number of different methodologies, could be sorted and used as separation complexes for FNLM separation using a device or system according to the present specification for analytes detection.

It will be appreciated that a system and method in accordance with the present teaching has a number of distinct advantages and can be employed in a number of different environments where magnetic forces may be used in analysis. The specifics of the arrangements may differ depending on the intended analysis target, for example protein, DNA, virus, bacteria, stem cells, etc. Use of the present teaching allows provision of highly sensitive bio-analytical assays and other methodologies where bio-separation may be advantageously employed in the understanding of living organisms. Therefore while it is not intended to limit the present teaching to any one specific methodology the following exemplary applications may be considered as indicative of tools that may employ the present teaching.

Specific use and implementation of the present teaching will depend on one of a number considerations including definition of a) assay protocol (e.g., monoclonal antibody, polyclonal antibodies, monoclonal-polyclonal antibody pair, or protein);

b) the matrix that the assay-separation has to be performed in (e.g., blood matrix, fermentation broth matrix, environmental matrix, etc);

c) if sensing can be done in a single step or if multiple steps are needed (i.e., some of these modes may require pre-concentration);

d) if fluorescent particles-magnetic particles or magnetic particle assemblies are preferred; and e) what users want to do with the particles after they are separated (for example if they are required for further use/analysis or may be discarded).

Example of Separation and Bio-sensing Applications for F-NLM:

1) Use of the present teaching allows rare cell separation from blood for translational medicine applications whereby magnetic separation is used in the isolation of rare cell types. One specific example is where stem cells are targeted. Having stem cells suspended in complex fluids like blood there is a need to isolate the stem cells. The stem cells are typically present in a very small fraction, i.e., 1:100,000 stem cell per blood cells. By using techniques employing the present teaching it is possible to provide a highly efficient separation protocol that is advantageously less stressful to the cells than for example centrifugation. An example of a protocol that may be employed in such a separation will be described as follows with reference to FIG. 10 A (the arrangement of the device shown is similar to that described with reference to FIGS. 5A and 6C):

a. In an initial step, one or more antibodies or receptors of choice are attached to super-paramagnetic particles. If large particles are used (>300 nm) the particles should be uniform in size (CV<30%) and magnetization (<30%). If small particles are used (<300 nm) the particles do not need to be as uniform in size or magnetization. Surface chemistries should minimize the nonspecific adhesion of proteins and/or nucleic acids.

b. The target analyte such as cells will be suspended in sample volumes that are 10-100 ml, viscous, and chemically unstable. Stabilizing agents (e.g., heparin). may need to be added to avoid coagulation and allow antibodies to react efficiently. The each of the magnetic particles will be mixed with the target analyte at a density of 10^5-10^9 particles/ml. The reaction will typically take place for 1-60 minutes. It may be useful c. Most of the antibodies used for stem cell separation are monoclonal and directed against cell surface proteins that are present in large numbers. Particle densities would need to be optimized to capture as many of the target cells as possible in the minimum time. Larger numbers of non-target cells and more viscous solutions would require longer reaction times or higher densities of particles. It will be noted that it may be preferable to mix the probes with the target analyte cells and then attach the magnetic particles to the target analyte using protein A or a similar receptor.

d. The F-NLM device would need to be able to work at relatively large flow rates in this case, i.e., flow rates of at least 1 ml/min of blood would be required. This means that continuous separation would be the most advantageous configuration, i.e, FIG. 5A or 6C. For example, this instrument may be made of glass-silicon, i.e., like a flow cytometer, but most biology labs like to work with plastic disposables.

e. Samples would need to be loaded onto the F-NLM magnetic array of the type shown in FIG. 5A. The particles would be loaded on the array and the external rotation frequency would be set so bare particles would be swept into channel 1161 leaving the stem cells on the chip (note that the is figure is a little confusing as it shows the separation of magnetic particles of two sizes). A single large micromagnet array or a small number of arrays (e.g., 1-5) would be preferred. The total number of micro-magnets would need to be at least 10× larger than the total number of cell-magnetic particle complexes to be collected. At the end of the separation either flow would be used to sweep the cells off the array into channel 1160 or the frequency would be reduced and the stem cells would be collected in channel 1161. This is of course not truly continuous separation because the feed would have to be stopped. Continuous separation could be achieved by running two or more channels in parallel for defined periods.

f. A practical issue of concern relates to non-specific adhesion of the blood proteins to the F-NLM separator and the need to capture the particles on the surface of the array. The first point can be addressed by adding stabilizing agents to the blood before separation and coating the surface of the chamber with non-ionic hydrophilic polymers that minimize nonspecific adhesion. The second point can be addressed by using a "force" to pull the particles down to the surface of the array just before separation. This force could be magnetic, hydrodynamic, or electrokinetic.

g. It may also be desirable to have a filter on the front of the separator to remove particle aggregates or cell debris. A particle counter on the flow streams may also be useful but this is not essential.

h. The example above is for a single cell type but it could be extended to multiple cell types if large magnetic particles were used.

i. The smaller particles would need to be used at higher densities so that the cells were given enough magnetic moment for separation. This would result in the binding on multiple particles to a single cell of interest but would also produce a cell-particle assembly with a distribution of magnetizations. This may be useful in identifying the density of receptors on a cell. Smaller magnetic particles may also be easier to remove from the cells of interest after separation.

Figure 10A:
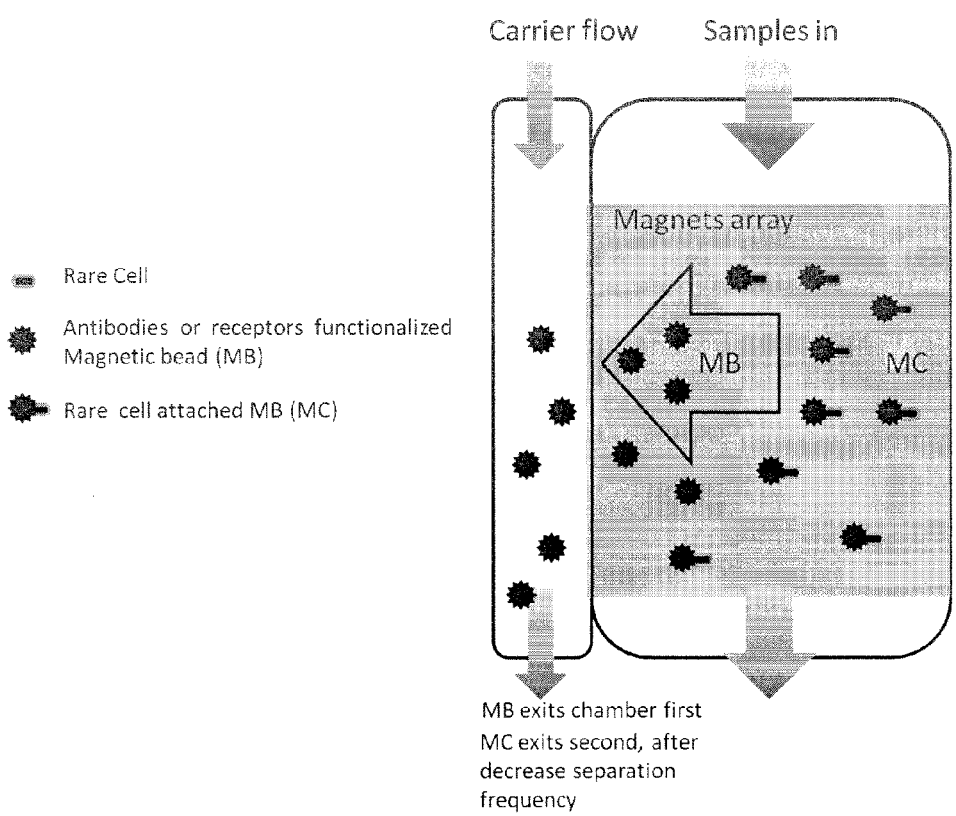
FIGS. 10A, 10B, 10C, 10D and 10E are illustrations of example separations using magnetic beads and a system and method of separation as provided by the present specification; in particular.
Figure 10B:
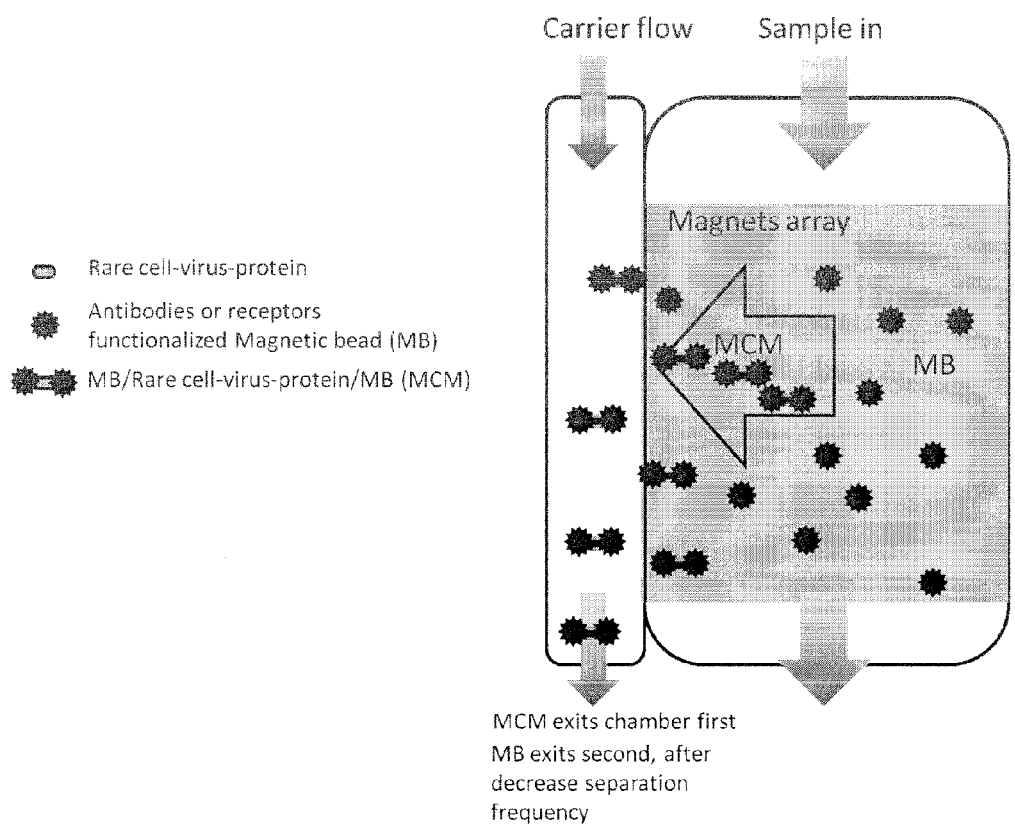
Figure 10C:
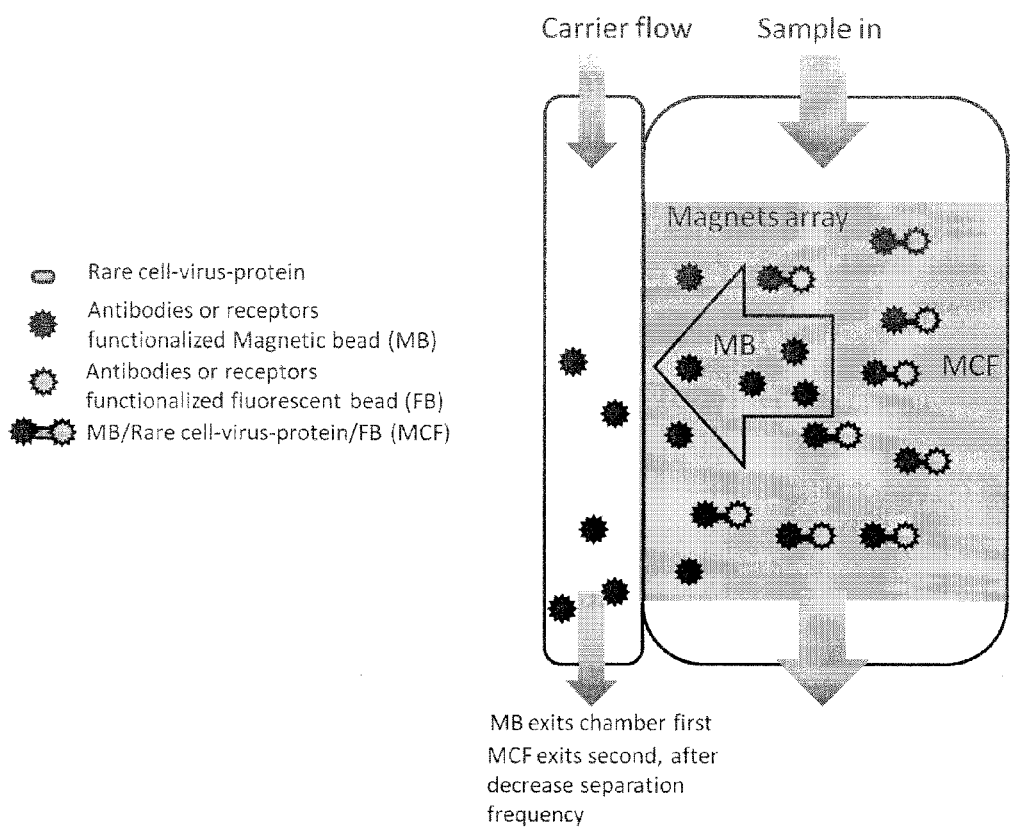

2) An example of a technique that may be employed in rare cell-virus-protein separation for diagnostics (double large magnetic particle, direct antibody configuration) is described in FIG. 10B (the arrangement of the device shown is similar to that described with reference to FIGS. 5A and 6C). An exemplary application where this may be usefully employed is identification of neonatal white blood cells that are in the mother's blood. This technique could also be used to identify bacteria and viruses for the identification of infectious diseases from complex media like blood. Small protein targets are also of interest, e.g, cardiac troponin I, which are present in blood but also in simpler media that comes from environmental sampling. Using a system and methodology in accordance with the present teaching it is possible to isolate these analytes which are present in a very small fraction, i.e., 1:100,000 cell per blood cells, using specific antibodies. The advantage of using F-NLM is that it is rapid, extremely sensitive, and can be used in a multiplexed sensing. The protocol would be as follows:

a. Attach one or more antibodies or receptors of choice to magnetic particles of defined size. The magnetic particles should be uniform in size (CV<30%) and magnetization (<30%). For smaller analytes, i.e., viruses and proteins, the particles should be smooth. Smaller analytes also have a smaller number of epitopes, which will change the manner in which the antibodies can be used. All surface chemistries should minimize the non-specific adhesion of proteins.

b. The analyte of interest would most likely be suspended in sample volumes that are 0.1-10 ml, viscous, and chemically unstable. Stabilizing agents may need to be added to avoid coagulation and allow antibodies to react efficiently, e.g., heparin. The each reacting particle type will be mixed with the cells at a density of $10^5$-$10^9$ particles/ml. In some cases, it may be desirable to mix the antibodies with the analyte and then attach the magnetic particles to the analytes using protein A or a similar receptor. The reaction will typically take place for 1-60 minutes.

c. It may be preferable to first separate the particles on a magnet using linear magnetophoresis to drive the clustering of magnetic particles around the analytes, which makes the complex easier to identify with F-NLM. It would be desirable if this step took place on the F-NLM device as it would make the sample handling easier and less prone to error.

d. After linear separation the sample will be moved to the F-NLM device. F-NLM would work at modest flow rates in this case because pre-concentration would reduce the working volume significantly, i.e., flow rates of t 0.1 ml/min would be sufficient. The sample would be identified through the formation of dimers and the most advantageous separation configuration would be a 2×2 continuous flow system (i.e., FIG. 5A or 6C). This instrument could be made of glass-silicon, i.e., like a flow cytometer, but most diagnostic labs like to work with plastic disposables.

e. Samples would be continuously loaded onto the F-NLM magnetic array, shown in FIG. 5A, and the external magnet rotation frequency would be set so the dimer particles would be swept into channel 1161 leaving the bare particles on the chip (note that the is figure is confusing as it shows the separation of magnetic particles of two sizes). The total number of micromagnetics would need to be at least 10× larger than the total number of bare magnetic particles to be collected. At the end of the separation or some intermediate point where the coverage of bare magnetic particles on the array is high flow would be used to sweep the bare magnetic particles off the array into channel 1160.

f. The practical issues identified with respect to the separation of rare cells will equally apply to this exemplary application, the separation of rare cell-virus-proteins g. The example above is for a single analytes but it could be extended to multiple analytes if different size magnetic particles were used.

h. A particle counter on the flow streams could be usefully employed for identifying the presence of the analytes. The use of an impedance type sensor would make it possible to identify the size of the aggregates and could be used as a filter for the assay in combination with frequency of external magnetic field rotation. An optical sensor could also be used to define the size of the particles is transmission mode. However, reflection and size scatter optical detectors could be used in conjunction with fluorescently labeled magnetic particles.

3) FIG. 100 (the arrangement of the device shown is similar to that described with reference to FIGS. 5A and 6C) shows a further exemplary application whereby rare cell-virus separation for diagnostics is effective using nonmagnetic-magnetic particles, direct protein configuration. One specific area where this could be employed is in targeting neonatal white blood cells that are in the mother's blood. This technique could also be used to identify bacteria or viruses for the identification of infectious diseases from complex media like blood. Small protein targets are also of interest, e.g, cardiac troponin I, which are present in blood but also in simpler media that comes from environmental sampling. By using a system and methodology in accordance with the present teaching it is possible to isolate these cells which are present in a very small fraction, i.e., 1:100,000 cell per blood cells, using specific antibodies. The advantage of using F-NLM is that it is rapid, extremely sensitive, and can be used in a multiplexed sensing. The protocol would be as follows:

a. Attach one or more antibodies or receptors of choice to magnetic or non-magnetic particles of defined size. The magnetic particles should be uniform in size (CV<30%) and magnetization (<30%). Nonmagnetic particles should have a uniform size (CV<10%) and it may be desirable if they are optically active. Surface chemistries should minimize the nonspecific adhesion of proteins. For smaller analytes, i.e., viruses and proteins, the particles should be smooth. Smaller analytes also have a smaller number of epitopes, which will change the manner in which the antibodies can be used.

b. The analyte of interest would most likely be suspended in sample volumes that are 0.1-10 ml, viscous, and chemically unstable. Stabilizing agents may need to be added to avoid coagulation and allow antibodies to react efficiently, e.g., heparin. The each reacting particle types will be mixed with the cells at a density of 10^5-10^9 particles/ml. The reaction will typically take place for 1-60 minutes.

c. A marked difference from Example 2 is that it may not be preferable to first separate the particles on a magnet using linear magnetophoresis as clustering would make multiplexed detection of more difficult. F-NLM would be performed at medium flow rates i.e., flow rates of t 0.1 ml/min would be sufficient. The sample would be identified through the formation of magnetic-nonmagnetic complexes and either a 2×2 continuous flow system (i.e., FIG. 5A or 6C) or simple flow configurations (6A, B, or D) would be suitable.

d. In this case, the magnetic conjugated particles will be captured on the F-NLM device while the nonmagnetic particles are flushed out of the device. This involves higher flow rates than in Example 2. The total number of micromagnetics would need to be at least 10× larger than the total number of magnetic particles. At the end of the first separation step the external magnet frequency would be set so the monomeric particles would be swept off the chip. After the monomers were removed either flow would be used to sweep the magnetic-nonmagnetic complexes off the array or the frequency would be reduced and the analyte would be collected.

e. Diagnostic assays can also be run with a linear magnetophoresis step. In this chase it is import to also count clusters of magnetic and nonmagnetic particles that will be promoted by the intimate contact created by linear magnetophoresis. These clusters will have a higher critical frequency and thus should be easily identified as the first set of magnetic particles that leave the chip.

f. The use of nonmagnetic particles brings the added benefit that if fluorescent particles are available they allow the analyte to be tagged for a second degree of sensitivity in multiplexed sensing.

h. A particle counter on the flow streams could be usefully employed for identification of the presence of the analytes. The use of an impedance type sensor would make it possible to identify the size of the aggregates and could be used as a filter for the assay in combination with frequency of external magnetic field rotation. An optical sensor could also be used to define the size of the particles is transmission mode. However, reflection and size scatter optical detectors could be used in conjunction with fluorescently labeled magnetic particles.

Figure 10D:
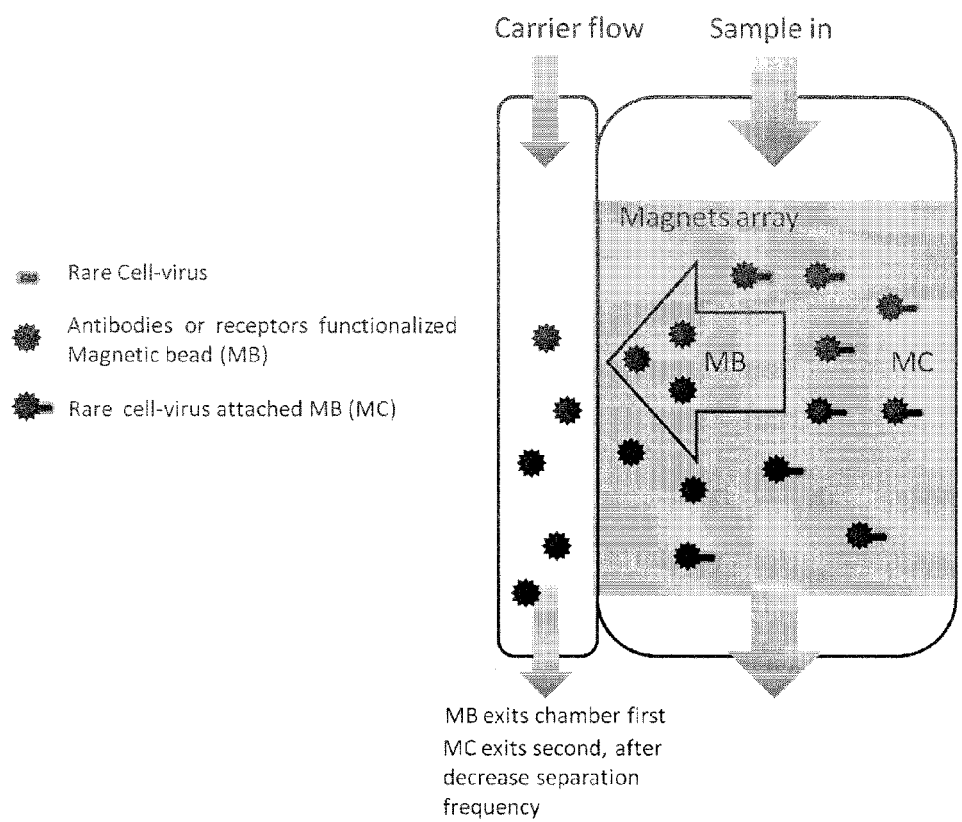

4) FIG. 10D (the arrangement of the device shown is similar to that described with reference to FIGS. 5A and 6C) shows in schematic form an arrangement that could be usefully employed in rare cell-virus separation for diagnostics using small magnetic particles and a direct protein configuration. The protocol would be as follows:

a. Attach one or more antibodies or receptors of choice to magnetic or nonmagnetic particles. Small particles are used (<300 nm) thus they do not need to be as uniform in size or magnetization as the large particles. However, it would be desirable if they were uniform in physical properties. Surface chemistries should minimize the nonspecific adhesion of proteins.

b. The cells of interest would most likely be suspended in sample volumes that are 0.1-10 ml, viscous, and chemically unstable. Stabilizing agents may need to be added to avoid coagulation and allow antibodies to react efficiently, e.g., heparin. The each reacting particle types will be mixed with the cells at a density of 10^5-10^9 particles/ml. The reaction will typically take place for 1-60 minutes. Note that it may be preferable to mix the antibodies with the cells and then attach the magnetic particles to the cells using protein A or a similar receptor.

c. It may be preferable to first separate the particles on a magnet using linear magnetophoresis. The purpose here would be to drive the clustering of magnetic particles around the cells, which would make the complex easier to identify with F-NLM. The smaller particles would need to be used at higher densities so that the cells were given enough magnetic moment for separation. This may be useful in identifying the density of receptors on a cell. Smaller magnetic particles may also be easier to remove from the cells of interest after separation. It would be desirable if this step took place on the F-NLM device as it would make the sample handling easier and less prone to error.

d. After linear separation the sample would be transferred in the F-NLM device. F-NLM would work at modest flow rates in this case because pre-concentration would reduce the working volume significantly, i.e., flow rates of t 0.1 ml/min would be sufficient. The sample would be identified through the shift in magnetization of the cell-bacteria-virus and the most advantageous separation configuration would be the 2×2 continuous flow system (i.e., FIG. 5A or 6C).

e. Samples would be continuously loaded onto the F-NLM magnetic array, such as the type shown in FIG. 5A, and the external magnet frequency would be set so the dimer particles would be swept into channel 1161 leaving the bare particles on the chip (note that the is figure is confusing as it shows the separation of magnetic particles of two sizes). At the end of the separation either flow would be used to sweep the bare magnetic particles off the array in channel 1160 or the frequency would be reduced to collect them in channel 1161. This is of course not truly continuous separation because the feed would have to be stopped.

Figure 10E:
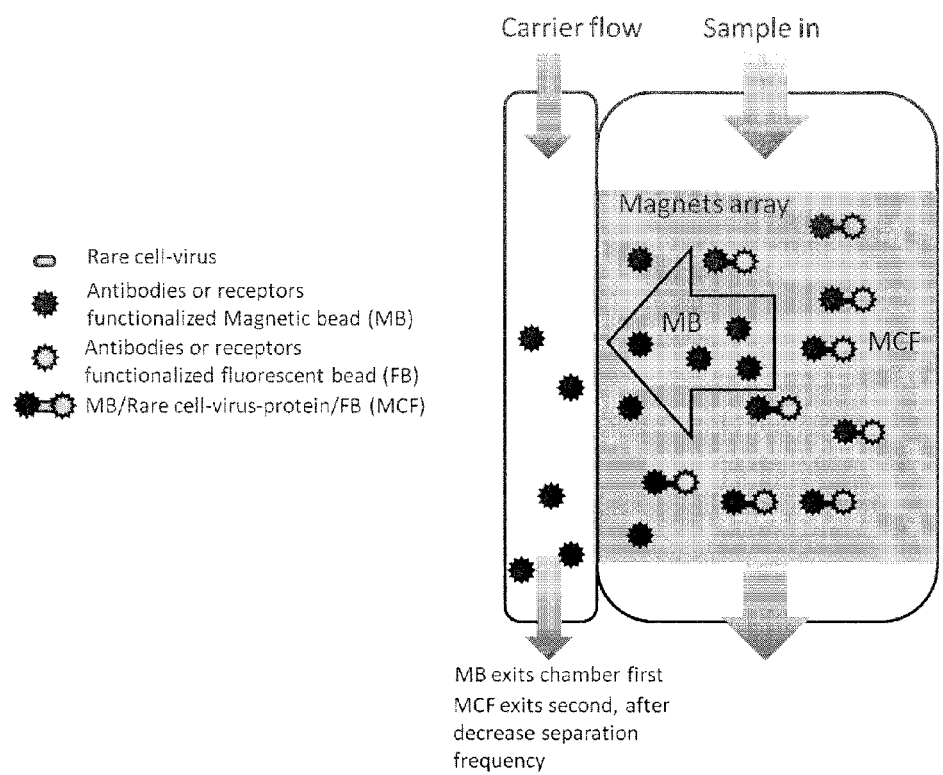

5) FIG. 10E shows a further application where the present teaching may be employed in rare cell-virus separation for diagnostics using magnetic-nonmagnetic or magnetic-magnetic particles in a molecular configuration. It is noted that the arrangement of the device shown is similar to that described with reference to FIGS. 5A and 6C. Molecular diagnostics have become a powerful and widely used tool for diagnosing diseases and these assays are highly successful because polymer chain reaction (PCR) amplification can be used to create large numbers of copies of the target nucleic acid (such as DNA) and the probes that are used for PCR provide an excellent degree of specificity. Disadvantages of the current generation of PCR include that it requires careful design of the probes and extraction of the nucleic acid (such as DNA) to overcome the deleterious effects of contamination. It also cannot be used to determine if the pathogen is viable. Use of techniques in accordance with the present teaching increases the speed and ease of separation as well as obviates the need for PCR amplification. This would be achieved by collecting pathogen using magnetic separation and then identification of specific sequences of the nucleic acid using the very high sensitivity of F-NLM. The protocol would be as follows:

a. Attach one or more antibodies, receptors, or nucleic acid oligonucleotides to magnetic or nonmagnetic particles. It would be desirable if all the particles are uniform in physical properties, i.e., magnetization, color and size. Surface chemistries should minimize the nonspecific adhesion of proteins.
b. The analyte of interest would most likely be suspended in sample volumes that are 0.1-10 ml, viscous, and chemically unstable. Stabilizing agents may need to be added to avoid coagulation and allow probes to react efficiently, e.g., heparin. The reacting particle types will be mixed with the cells at a density of 10^5-10^9 particles/ml. The reaction will typically take place for 1-60 minutes. It will be noted that it may be preferable to mix the probes with the target analyte cells and then attach the magnetic particles to the target analyte using protein A or a similar receptor.
c. It may be preferable to first separate the particles on a magnet using linear magnetophoresis. The purpose here would be to clean-up the sample for DNA extraction. After linear separation the nucleic acid would be extracted, hybridized with specific oligonucleotides, and then reacted with a second set of particles. It would be desirable if these steps took place on the F-NLM device as it would make the sample handling easier and less prone to error.
d. The sample could be identified through the formation of magnetic-magnetic complexes. The most advantageous separation configuration for aggregates would be the 2×2 continuous flow system (i.e., FIG. 5A or 6C). F-NLM would work at modest flow rates in this case because pre-concentration would reduce the working volume significantly, i.e., flow rates of t 0.1 ml/min would be sufficient. The sample would be continuously loaded onto the F-NLM magnetic array and the external magnet frequency would be set so the dimer particles would be swept into channel 1161 leaving the bare particles on the chip. At the end of the separation either flow would be used to sweep the bare magnetic particles off the array into channel 1160 or the frequency would be reduced to collect them in channel 1161.
e. The sample could be identified through the formation of magnetic-optical complexes. The separation protocol is described in Example 3 above.
f. The example above is for a single analyte type but it could be extended to multiple types of analytes of different size magnetic and/or optical particles were used.

Figure 11A:
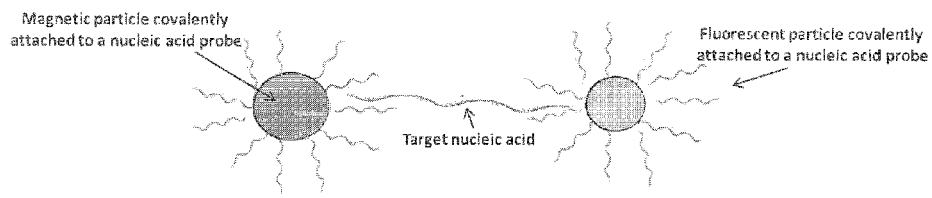
FIGS. 11a, 11b and 11c show examples of tagged particles that may be usefully employed within the context of the present teaching.
Figure 11B:
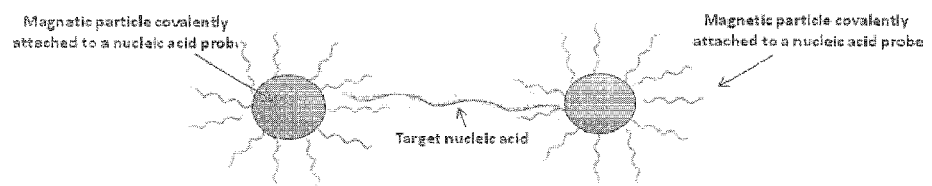
Figure 11C:
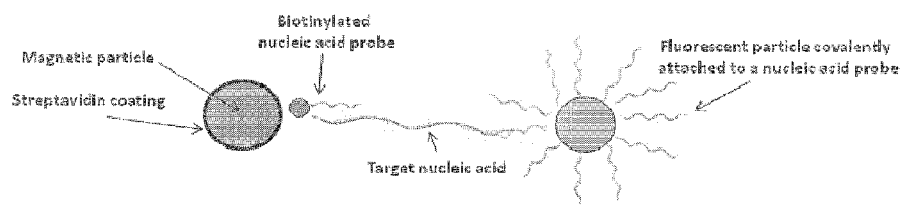

FIGS. 11*a*, 11*b* and 11*c* show examples of particles that can be analysed using a system in accordance with the present teaching. In the examples, the particle assembly is via nucleic acid interactions with subsequent NLM detection. In the arrangement of FIG. 11*a*, magnetic particles covalently attached to a nucleic acid probe form complexes with a second fluorescent particle also covalently attached to a nucleic acid probe. In FIG. 11*b*, a similar arrangement is provided however a second magnetic particle as opposed to a fluorescent particle is covalently attached to a nucleic acid probe. In FIG. 11*c*, an example of a streptavidin coated magnetic particle is coupled to a biotinylated nucleic acid probe forming complexes with a second fluorescent (which similarly to FIG. 11*b* could also be a magnetic particle) also covalently attached to a nucleic acid probe. It will be appreciated that in each of these configurations:

The magnetic and fluorescent particles can be of any size
The fluorescent particles can be of any fluorescence
The nucleic acid probes can be DNA or RNA
The nucleic acid probes can contain degenerate bases
The nucleic acid probes can be of varying length
The nucleic acid probe can contain any ligand complementary to the surface of the magnetic or fluorescent particles.

It will be appreciated these specific types of particles while useful in the context of F-NLM could also be advantageously used with other types of magnetic separators. Experimental evidence shows that using such particles that it is possible to capture genomic DNA through the formation of complexes using nucleic acid probes and magnetic particles. It will be understood that this is only an example of the type of capture that could be performed using these types of complex particle structures. For example by suitably configuring the particles it is possible to provide mRNA isolation and the capture of primary or secondary antibodies.

Figure 12:
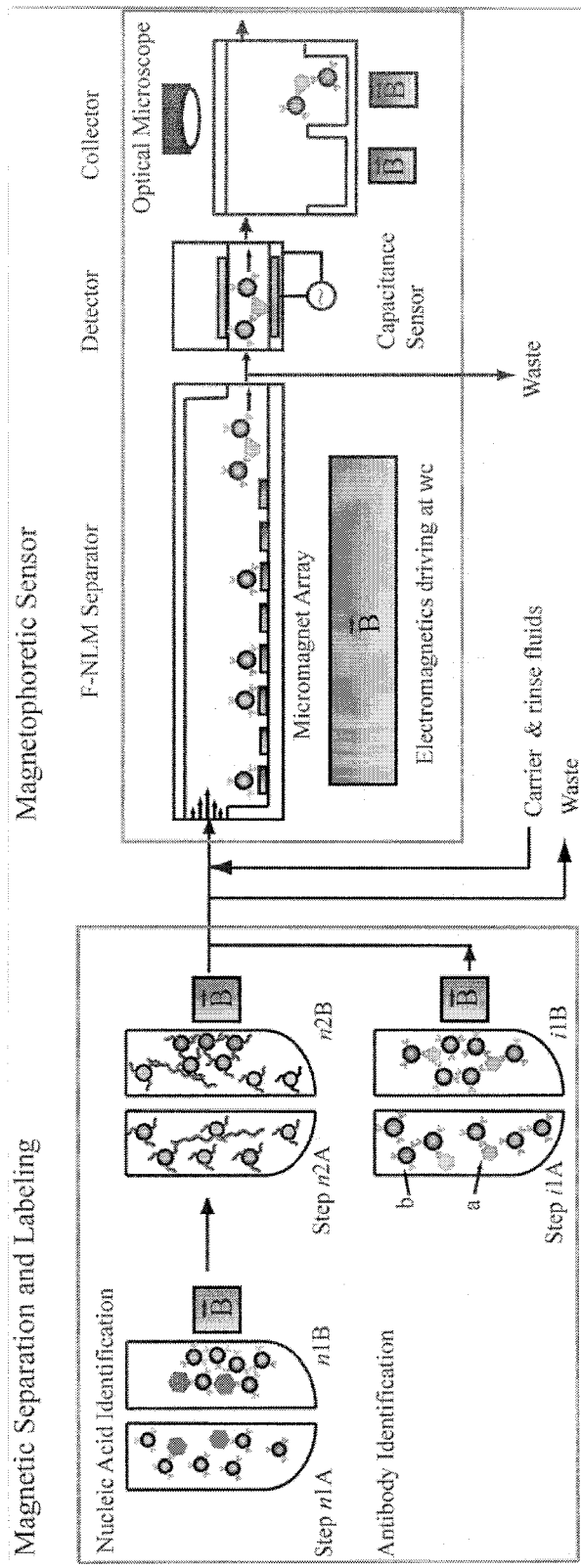
FIG. 12 shows an example of how the system of FIG. 4b may be incorporated into a larger analysis system.

As discussed above the F-NLM separator of the present teaching can be provided in-line within a larger analysis system comprising one or more of an aggregator and a detector sub-system. FIG. 12 shows such an example where a system module such as previously described with reference to FIG. 4*b* is incorporated into a larger analysis system. In this configuration the F-NLM separator is provided downstream of a magnetic separation and labelling module and upstream of detector and collector modules.

In the example of FIG. 12 the magnetic separation and labelling module describes two alternative analysis techniques that may be usefully employed within the context of the present teaching. In the first—Step n1A, n1B, n2A, n2B nucleic acid identification is provided. In this schematic the n1 blocks reflect the stripping out of the nucleic acid from an initial sample and the n2 blocks reflect a further processing to tag those stripped particles to magnetic particles or the like for use in the downstream F-NLM analysis. The Step i1A blocks show an equivalent pre-processing for antibody identification.

Figure 13:
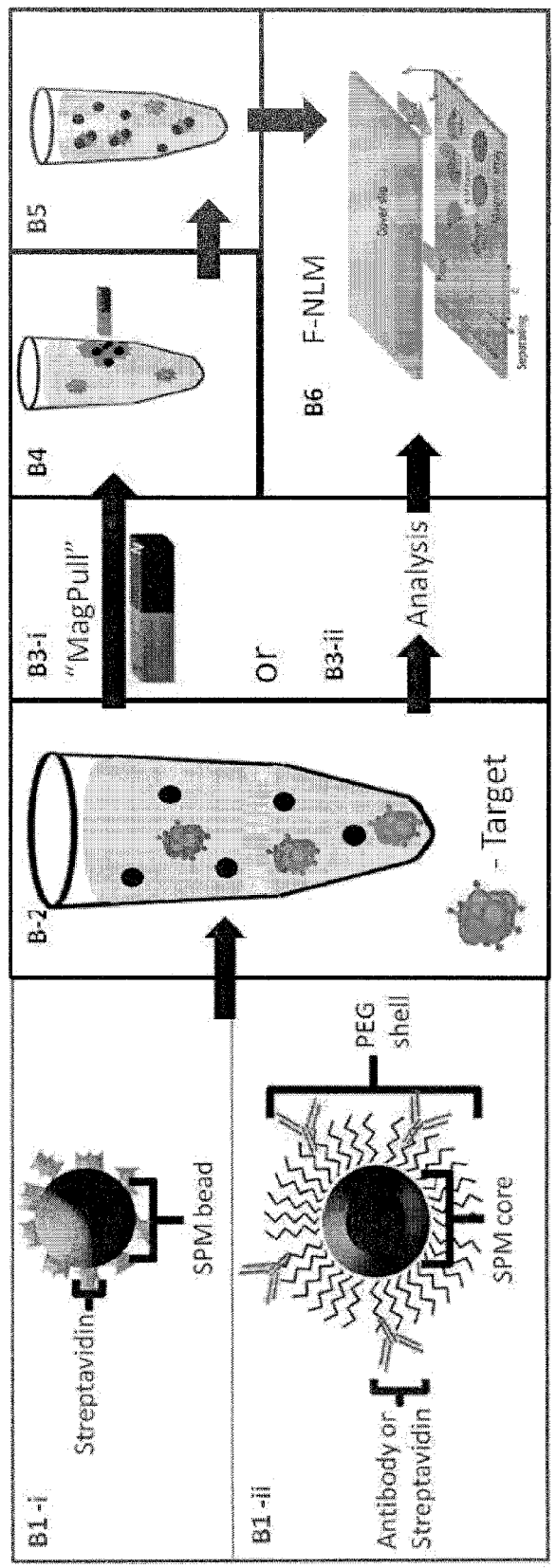
FIG. 13 shows an example of an upstream aggregation technique that may be usefully employed as part of the magnetic separation and labelling module of FIG. 12.

FIG. 13 shows an example of an upstream assay operation using super-paramagnetic materials (SPM's). The specifics of the operation will depend on the assay time and bead concentrations the aggregates can be large and contain numerous super-paramagnetic materials (SPM's). In this example which provides two initial starting particles as exemplary of the type of analysis that may be conducted a number of steps are completed as part of a magnetic separation and labelling. This detail is exemplary of the type of analysis that may be conducted as part of the i1A steps of FIG. 12.

B1—SPM's are either (i)—purchased with a streptavidin functionality, or (ii) carboxyl beads from the same supplier are covered with a PEG coating that is later conjugated to the protein of choice.
B2—SPM's are incubated with target.
B3i—Aggregation of the beads is aided via the use of a "magpull" stage, or if required
B3-ii the sample can be analysed immediately by passing it downstream for further analysis.
B4—During the "magpull" stage the beads may be washed.
B5—Beads are resuspended before analysis which will be conducted as part of a downstream analyser.
B6i—The aggregated particles are provided downstream to an F-NLM analyser or if used independently of same to another analyser to allow for further analysis. This can be used to count the number of bead aggregates.

It will be appreciated that the above steps comprise the sequential exposure of beads to magnetic fields of different orientations. Effectively in the second step the relative orientation of the beads to the field is varied. This may be achieved through use of moving the beads relative to the magnetic field or maintaining the beads stationary and varying the direction of the applied field.

In step B3-i—the MagPull step, the sample was left in the presence of a magnetic field until all the beads were judged to have come out of solution (1 min), the initial solution was removed leaving all the beads on the side of the container and 500 μl PBS was added to the beads. The solution was stirred and the magnet was replaced and the beads separated out under the magnetic field for a second time. Once the SPMs had collected onto the side of the container the tube was rotated 90 degrees, whilst maintaining the magnetic field. This allowed the pellet of SPMs to roll over the side of the container and each other until they had settled over the magnet again, at this stage the magnet was removed and the pellet was allowed to settle to the bottom of the vial for 30 sec before finally being vortexed, resuspended and diluted into 1 ml of PBS for analysis. This process we term "Magpull" and is aimed to increase the particle-particle interactions and thus increase the number of particle aggregates.

Figure 14:
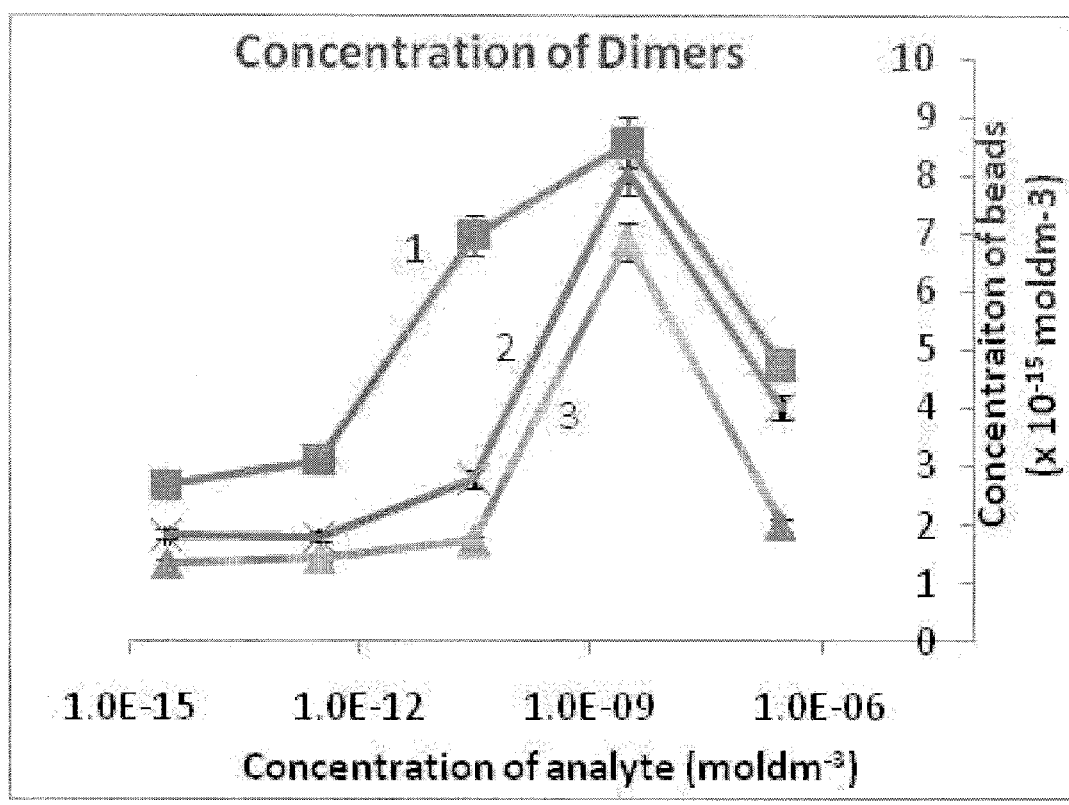
FIG. 14 shows exemplary data indicative of the improvement possible using the aggregation technique of FIG. 13.

In conducting further analysis of the effect of this Magpull stage it was noticed that after being incubated with the analyte for 30 min that the beads were close to being saturated. Further analysis indicated that this saturation most likely occurs within the first few minutes. Indeed experimental data such as the result shows in FIG. 14, which shows Concentration of dimers in an assay as a function of analyte concentration, 1-30 min assay magpull, 2-5 min assay magpull, 3-5 min assay no magpull it is clear that only minor changes in the aggregates numbers are observed when the assay time is reduced. The fact that there exists a relatively low efficiency in relationship between aggregates and analyte concentration means that this technique provides a signal, over eight orders of magnitude. The use of the magpull to effect the number of dimers at longer hybridization times is minimum when the concentrations of analyte is high, but can be seen to cause an increase for formation of dimers at lower concentrations, curve 2—FIG. 14. The samples in some assays was analysed prior to the magpull (curve 3—FIG. 14) similar curves are observed, however in these samples the number of dimers and larger aggregates depends upon the collision frequency of the beads in solution. At high concentrations the curves correlate with those of the magpull experiment, but the number of measured aggregates in the presence of the magpull was always greater It will be appreciated that the system and methodology described heretofore has a number of advantages over prior art techniques. These include the ability to provide separation without having to apply the high magnetic field gradients that have been required in the prior art approaches. The system and methodology is also simplified in comparison with the prior art approaches.

The separation provided in frequency dependent which provides for multiple sensing and is easily integrated with automatic control system to provide high levels of flexibility of application.

The separation device advantageously provides for separation of multiple analytes such as for example, for separation/detection of analytes attached with particles, such as macro-organism, DNA, antibodies.

By introducing flow into non-linear magnetophoretic separations it is possible to provide for manipulation of particles based on particle behaviour by adjusting flow and the external magnetic field within the device to enable a continuous non-linear magnetophoretic separation and to provide for multiple separations of multiple particles. It will be appreciated that the present teaching takes advantages of known benefits of magnetophoresis in using the motion of dispersed magnetic particles relative to a fluid under the influence of a magnetic field to detect or isolate specific components in the fluid using specific binding and or capture. By introducing flow into a magnetophoretic separator the present teaching provides an improved use of magnetic beads in a detection and purification of DNA, proteins and antibodies.

The device, system and method of the present specification provide for frequency dependent separation which may be easily integrated and implemented in a digital arrangement. This provides a two tier system and method for the separation of beads based on their physical properties. In summary, F-NLM system and method of the present specification have a number of advantages over prior art approaches 1) it can be used to work with a relatively high density of magnetic beads in milliliter volumes;
2) it has all the advantages inherent to chip based technologies;
3) $\Omega_t$ is proportional to bead size and has a range of frequency dependence that is larger than the range observed in prior art NLM; and
4) the velocity of the beads at the edge of the micromagnet array was proportional to bead size and thus can also be used for separation.

In this way the present teaching may be employed to rapidly separate multiple analytes bound to super-paramagnetic beads from milliliter volume samples. Whereas prior art techniques allows for separation of super-paramagnetic micro-particles based on their size and magnetic moment by using non-linear magnetophoresis (NLM), the present teaching combines this with provision of a flow field substantially perpendicular to the orientation of the applied external magnetic field. The traditional NLM transport behavior on the micro-magnet array is maintained at low fluid velocities but particles will simultaneously move in the direction of the flow at a velocity that is determined by the flow rate and the applied field frequency. By tuning the external field frequency and the flow rate it is possible to cause migration velocities of different bead types to differ by several orders of magnitude over an extended range of frequencies. In this way it is possible to separate super-paramagnetic particles with 95% efficiency. Use of such efficiency in separation allows for application in bio-separation and similar assays.

Various alternative arrangements of the device and system have been described. It will be appreciated that the device and system may be provided or manufactured in various configurations without departing from the scope of the invention. For example, the detector, monitoring and sensor means may be provided integrated into a single chip device or for connection in series. For example, components of the device or system may be provided as sterile or single-use or disposable components while other components may be provided for re-use, as required.

The words comprises/comprising when used in this specification are to specify the presence of stated features, integers, steps or components but does not preclude the presence or addition of one or more other features, integers, steps, components or groups thereof.

The invention claimed is:

1. A separation system for flow enhanced non-linear magnetophoretic separation of magnetic particles of a first and second type of a sample, comprising:
   a chip assembly device comprising:
      a flow chamber having an inlet for the introduction of the sample as a flowing sample and an outlet, the flow chamber having a flow path in a first direction between the inlet and the outlet, the flow path comprising a first fluid path and a second fluid path located side by side and having fluid communication therebetween to allow for magnetic particles of the first and second type to be transported from the first fluid path to the second fluid path, and a micro magnet array provided in the first fluid path defining a magnetic separation fluid path;

the second fluid path defining a flow separation channel;

a flow controller configured to apply flow to the flow chamber such that the particles within the sample travelling in the first and second fluid paths experience hydrodynamic forces affecting their movement in the direction of the flow path, wherein the flow controller provides control of the rate of the flow in each of the first and second fluid paths and wherein the flow is applied continuously;

a magnetic module comprising electromagnets and a controller, the magnetic module configured to apply a rotating magnetic field to the first fluid path of the chip assembly device such that particles within the sample travelling in the first fluid path operably experience an induced magnetic field based on interaction of the rotating magnetic field and the magnetic field of first micro magnet array proximal the first fluid path; the magnetic module further configured to apply the rotating magnetic field in a second direction, substantially perpendicular to the direction of flow, and the rotating magnetic field is selected to effect transport of particles of the second particle type from the first fluid path to the second fluid path; and a system controller, wherein taking account of the properties of the particles of the first type and second type, and the critical and threshold frequencies at which the particles of the first and second type are responsive to the rotating magnetic field, the system controller is configured to:

(1) control the frequency of the rotating magnetic field, and (2) control the rate of flow of the sample in the first fluid path wherein the frequency of the rotating magnetic field and the rate of flow of the sample are tuned relative to each other to effect a retention of particles of the first type in the first fluid path and transport of particles of the second type to the second fluid path and to provide separation of the particles of the first type from particles of the second type in the first fluid path.

2. The system as claimed in claim 1 wherein the particles of the first and second type are responsive to a predefined frequency of operation of the rotating magnetic field, the particles of the first type having a critical frequency, $\omega_c$ at which particles of the first type are trapped in the micro magnet array, the particles of the first type having a threshold frequency $\Omega_t$ at which a majority of particles of the first type are trapped in the micro magnet array, the micro magnet array being tuneable to allow selection of at least one of the critical and threshold frequency.

3. The system of claim 2 wherein the particles of the second type have a different critical and threshold frequency to the particles of the first type.

4. The system of claim 2 wherein the threshold frequency is greater than the critical frequency for each of the particles of the first and second types.

5. A system as claimed in claim 1 wherein the frequency $\omega$ of the rotating magnetic field is greater that the critical frequency $\omega_c$ of the particles of the first type and less than the critical frequency $\omega_c$ of the particles of the second type.

6. A system as claimed in claim 1 wherein each of the flow control and the magnetic control effects a variance in an induced force on the particles within the device and wherein each of the flow control and magnetic control are tuneable to effect separation of the particles of the first and second types.

7. A system as claimed in claim 1 wherein the frequency of the rotating magnetic field is controllable to effect transport of the particles of the second type to an intermediary region adjacent to each of the first and second fluid paths in the direction of the rotating magnetic field.

8. A system as claimed in claim 7 wherein the rate of flow in the second fluid path is operably controlled to provide a hydrodynamic force to effect movement of the particles of the second type which have been transported to an intermediary region adjacent to each of the first and second fluid paths.

9. A system as claimed in claim 7 wherein the frequency of rotation of the external magnetic field is controllable to operably provide that particles of the second type oscillate in phase with the external magnetic field at the intermediary region.

10. A system as claimed in claim 1 wherein the flow controller effects a variance on the flow based on properties of the particles of the first and/or second type.

11. A system as claimed in claim 1 further comprising a sensor or detector configured to sense or detect particles wherein the sensor or detector comprises an impedance sensor, a micro-coulter detector, an optical microscope, or a fluorescent detector.

12. A system as claimed in claim 1 configured for use in-line with linear magnetophoresis, the linear magnetophoresis effecting a first separation of particles.

13. A system as claimed in claim 1 wherein the particles are provided in the form of micro-beads and/or wherein the particles are functionalised prior to introduction into the chip-assembly device.

14. A system as claimed in claim 1 wherein the frequency of rotation and flow rate are controllable to provide a continuous separation.

15. A method of flow-enhanced non-linear magnetophoretic separation of magnetic particles of a first and second type of a sample, the method comprising:

providing a separation system in accordance with claim 1 comprising a chip assembly device including a first fluid path comprising a micro magnet array and a second fluid path comprising a flow separation channel, an electro magnet, and a flow controller;

introducing a sample including particles of the first and the second type to be separated into the system;

applying flow continuously to the sample in the chip assembly device;

applying a rotating magnetic field proximate to the first fluid path;

controlling the frequency of the rotating magnetic field, controlling the rate of flow in the first fluid path;

wherein the frequency of the rotating magnetic field and the rate of flow are tuned relative to each other to effect a retention of particles of the first type in the first fluid path and to transport particle of the second type to the second fluid path to provide separation of said particles of the second type from said particles of the first type.

16. A method as claimed in claim 15 further comprising controlling the rate of flow in first and second fluid paths.

17. A method as claimed in claim 15 further comprising operating the rotating magnetic field at a frequency of rotation above the critical frequency of the particles of the first type and below a threshold frequency of particles of the second type to effect a separation thereof.

18. A method as claimed in claim 17 further comprising transporting the particles of the second type across the first fluid path comprising a micro-magnet array to the second fluid path comprising a non-magnetic separation channel adjacent an edge of the first fluid path.

19. A method as claimed in claim 17 further comprising applying a non-magnetic force to transport particles of the second type downstream in the second fluid path from said edge of the first fluid path to effect separation of said particles of the second type.

20. A method as claimed in claim 19 further comprising applying flow and controlling the rate of flow of the sample in the chip assembly device such that the resultant hydrodynamic forces effect transport and separation of said particles of the second type.

21. A method as claimed in claim 18 wherein the rate of flow is controlled such that the induced hydrodynamic force is in a range less than the force needed to displace the particles of the first type trapped on the micro-magnet array in the first fluid path and greater than that need to displace particles of the second type which have been transported to the edge of the micro-magnet array in the first fluid path.

22. A method as claimed in claim 21 wherein after the particles of the second type have been separated from the particles of the first type and transported downstream by flow, the frequency of rotation is reduced to a frequency below the critical frequency of the particles of the first type to effect transport by non-linear magnetophoresis of the particles of the first type to the edge of the micro-magnet array of the first fluid path and to the second fluid path and transport of the particles of the first type downstream in the second fluid path.

23. A method as claimed in claim 22 wherein after particles of the second type have been separated the rate of flow is controlled such that the induced hydrodynamic force in the micro-magnet array of the first fluid path is sufficient to displace and transport said particles of the first type downstream in the first fluid path.

24. A method as claimed in claim 21 further comprising collecting or counting or analysing said first and particles of the second type that have been separated.

25. A method as claimed in claim 15 wherein the frequency of rotation and flow rate are controlled to provide a continuous separation.

26. A method of flow enhanced non-linear magnetophoretic separation as claimed in claim 15 further comprising separating rare cell for translation medicine applications including stem cell separation from a complex fluid sample.

27. A method as claimed in claim 26 wherein the sample comprises cell-magnetic particles complexes to be separated.

28. A method as claimed in claim 26 further comprising attaching one or more antibodies or receptors of choice to super-paramagnetic particles prior to introducing the sample to the separation system.

29. A method of flow enhanced non-linear magnetophoretic separation as claimed in claim 15 further comprising attaching analytes of interest to be separated to selected magnetic particles of defined size to at least one of;
rare cell-virus-protein separation for diagnostics; or
separate neonatal white blood cells from a maternal blood sample.

30. A method as claimed in claim 29 further comprising firstly separating the particles on a magnet using linear magnetophoresis to drive the clustering of magnetic particle around analytes to provide increased ease of identification of complexes in the subsequent step of non-linear magnetophoretic separation.

31. A method as claimed in claim 15 further comprising separating rare cell-virus for diagnostics using nonmagnetic-magnetic particles in a direct protein configuration to separate neonatal white blood cells from a sample of maternal blood.

32. A method as claimed in claim 31 further comprising preparing the sample for separation by attaching one or more antibodies or receptors of choice to magnetic or non-magnetic particles of defined size.

33. A method as claimed in claim 32 wherein the non-magnetic particles comprise fluorescent particles configured to allow an analyte to be tagged for a second degree of sensitivity in multiplexed sensing.

34. A method as claimed in claim 32 wherein the sample is identified through formation of magnetic-nonmagnetic complexes.

35. A method as claimed in claim 15 further comprising;
separating rare cell-virus for diagnostics using small magnetic particles and a direct protein configuration further comprising;
attaching one or more antibodies or receptors of choice to magnetic or nonmagnetic particles; and
mixing the antibodies with the cells prior to attaching the magnetic particles to the cells using a protein or similar receptor.

36. A method as claimed in claim 15 further comprising, prior to introducing the sample comprising beads of a first and a second type, aggregating a plurality of beads.

37. The method of claim 36 wherein the aggregating a plurality of beads comprises:
providing a container with a sample solution with beads in the presence of a magnetic field of a first orientation;
allowing the beads to migrate to and collect on a side surface of the container; and
exposing the beads to a magnetic field of a second orientation to allow formation of aggregates of the beads.

38. The method of claim 37 comprising subsequent to the collection of the beads on a side surface of the container, replacing the sample solution with a second solution and re-exposing the second solution to a magnetic field to allow the beads to migrate to and collect on the side surface of the container.

39. The method of claim 37 wherein the beads are super-paramagnetic beads.

40. A method as claimed in claim 35 further comprising separating the particles on a magnet using linear magnetophoresis prior to flow enhanced non-linear magnetophoretic to drive the clustering of magnetic particles around the cells.

41. A method as claimed in claim 15 further comprising separating rare cell-virus for diagnostics using magnetic-nonmagnetic particles in a molecular configuration.

42. A method of claim 41 further comprising attaching one or more antibodies, receptors, or DNA oligonucleotides to magnetic or nonmagnetic particles, and wherein the particles are preferably uniform in physical properties including at least one of magnetization, color and size.

43. A method as claimed in claim 41 further comprising separating the particles on a magnet using linear magnetophoresis to clean-up the sample for DNA extraction, and after linear separation extracting the DNA and hybridizing with specific oligonucleotides and then reacting with a second set of particles prior to flow enhanced non-linear magnetophoretic separation.

44. A method as claimed in claim 41 wherein the sample is identified through the formation of magnetic-magnetic complexes and/or through the formation of magnetic-optical complexes.

* * * * *